United States Patent
Lamego et al.

(10) Patent No.: US 8,571,618 B1
(45) Date of Patent: Oct. 29, 2013

(54) ADAPTIVE CALIBRATION SYSTEM FOR SPECTROPHOTOMETRIC MEASUREMENTS

(75) Inventors: Marcelo Lamego, Coto De Caza, CA (US); Sean Merritt, Lake Forest, CA (US); Massi Joe E. Kiani, Laguna Niguel, CA (US)

(73) Assignee: Cercacor Laboratories, Inc., Irvine, CA (US)

( * ) Notice: Subject to any disclaimer, the term of this patent is extended or adjusted under 35 U.S.C. 154(b) by 347 days.

(21) Appl. No.: 12/891,428

(22) Filed: Sep. 27, 2010

Related U.S. Application Data

(60) Provisional application No. 61/246,288, filed on Sep. 28, 2009, provisional application No. 61/257,722, filed on Nov. 3, 2009.

(51) Int. Cl.
*A61B 5/1455* (2006.01)

(52) U.S. Cl.
USPC .......................... 600/316; 600/310; 600/322

(58) Field of Classification Search
USPC ................................................ 600/309–344
See application file for complete search history.

(56) References Cited

U.S. PATENT DOCUMENTS

| | | | |
|---|---|---|---|
| 4,960,128 A | 10/1990 | Gordon et al. | |
| 4,964,408 A | 10/1990 | Hink et al. | |
| 5,041,187 A | 8/1991 | Hink et al. | |
| 5,068,536 A * | 11/1991 | Rosenthal | 250/341.5 |
| 5,069,213 A | 12/1991 | Polczynski | |
| 5,163,438 A | 11/1992 | Gordon et al. | |
| 5,319,355 A | 6/1994 | Russek | |
| 5,337,744 A | 8/1994 | Branigan | |
| 5,341,805 A | 8/1994 | Stavridi et al. | |
| D353,195 S | 12/1994 | Savage et al. | |
| D353,196 S | 12/1994 | Savage et al. | |
| 5,377,676 A | 1/1995 | Vari et al. | |
| D359,546 S | 6/1995 | Savage et al. | |
| 5,431,170 A | 7/1995 | Mathews | |
| D361,840 S | 8/1995 | Savage et al. | |
| D362,063 S | 9/1995 | Savage et al. | |
| 5,452,717 A | 9/1995 | Branigan et al. | |
| D363,120 S | 10/1995 | Savage et al. | |
| 5,456,252 A | 10/1995 | Vari et al. | |

(Continued)

OTHER PUBLICATIONS

"Diabetes: Choosing and Using your Glucose Meter", MedicineNet. com, http://www.medicinenet.com/script/main/art. asp?articlekey=20554&pf=3&page=1, accessed on Sep. 22, 2009, 10 pages.

(Continued)

*Primary Examiner* — Eric Winakur
*Assistant Examiner* — Marjan Fardanesh
(74) *Attorney, Agent, or Firm* — Knobbe Martens Olson & Bear LLP

(57) ABSTRACT

This disclosure describes, among other features, systems and methods for customizing calibration curves, parameter algorithms, and the like to individual users. An initial calibration curve generated based on a population can be used as a starting point in an algorithm for measuring a physiological parameter such as glucose. The measurement algorithm can determine one or more initial measurement values for a user based on the initial calibration curve. In certain embodiments, one or more alternative measurements, such as invasive or minimally invasive measurements, can periodically or sporadically be input into the measurement algorithm. The algorithm can use the alternative measurements to adapt the calibration curve to the individual. As a result, measurements for the individual can more accurately reflect the individual's actual parameter values.

18 Claims, 14 Drawing Sheets

(56) References Cited

U.S. PATENT DOCUMENTS

| | | |
|---|---|---|
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,507,288 A * | 4/1996 | Bocker et al. .................. 600/322 |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-All |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |

(56) References Cited

U.S. PATENT DOCUMENTS

| | | |
|---|---|---|
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 2002/0016535 A1 | 2/2002 | Martin et al. |
| 2004/0225205 A1 * | 11/2004 | Fine et al. ............ 600/316 |
| 2006/0229531 A1 | 10/2006 | Goldberger et al. |

OTHER PUBLICATIONS

Ni et al., "Simultaneous Spectrophotometric Determination of Maltol, Ethyl Maltol, Vanillin and Ethyl Vanillin in Foods by Multivariate Calibration and Artificial Neural Networks", Food Chemistry, 89:465-473, (2005).

Mendosa, "The GlucoWatch Biographer", http://www.mendosa.com/glucowatch.htm, accessed on Sep. 22, 2009, 4 pages.

* cited by examiner

ADAPTIVE CALIBRATION SYSTEM FOR SPECTROPHOTOMETRIC MEASUREMENTS

RELATED APPLICATIONS

This application claims priority from U.S. Provisional Patent Application No. 61/246,288 filed Sep. 28, 2009, entitled "Adaptive Calibration System for Spectrophotometric Measurements," and from U.S. Provisional Patent Application No. 61/257,722, filed Nov. 3, 2009, entitled "Adaptive Calibration System for Spectrophotometric Measurements," the disclosures of both of which are hereby incorporated by reference in their entirety.

BACKGROUND

The standard of care in caregiver environments includes patient monitoring through spectroscopic analysis using, for example, a pulse oximeter. Devices capable of spectroscopic analysis generally include a light source(s) transmitting optical radiation into or reflecting off a measurement site, such as, body tissue carrying pulsing blood. After attenuation by tissue and fluids of the measurement site, one or more photodetection devices detect the attenuated light and output one or more detector signals responsive to the detected attenuated light. A processor can process the one or more detector signal and output a measurement reflective of a blood constituent of interest, such as glucose, oxygen, methemoglobin, total hemoglobin, among other physiological parameters.

In noninvasive devices and methods, a sensor is often adapted to position an appendage such as a finger proximate a light source and a light detector. For example, noninvasive sensors often include a clothespin-shaped housing that includes a contoured bed conforming generally to the shape of a finger.

SUMMARY OF CERTAIN EMBODIMENTS

This disclosure describes embodiments of noninvasive methods, devices, and systems for measuring a blood constituent or analyte, such as oxygen, carbon monoxide, methemoglobin, total hemoglobin, glucose, proteins, lipids, a concentration percentage thereof (e.g., saturation), or for measuring many other physiologically relevant patient characteristics. These characteristics can relate, for example, to pulse rate, hydration, trending information and analysis, patient wellness, and the like.

In certain embodiments, a device capable of producing a signal responsive to light attenuated by tissue at a measurement site includes an optical sensor that can emit light on tissue of a living person, detect the light after attenuation by the tissue, and output a signal responsive to the attenuated light. The device can further include a processor that can receive the signal from the optical sensor, process the signal with a measurement algorithm to determine a first measurement of a physiological parameter, receive a second measurement of the physiological parameter from an alternative source, and adaptively adjust the measurement algorithm based at least partly on the second measurement.

In certain embodiments, a method of determining whether to recommend an alternative measurement of a physiological parameter can include obtaining a noninvasive measurement of a physiological parameter using an optical sensor, receiving an alternative measurement of the physiological parameter, where the alternative measurement can be generated by an alternative sensor, analyzing the noninvasive and alternative measurements to determine whether a condition has been met, and in response to the condition being met, outputting an indication that a new measurement should be obtained from the alternative sensor.

For purposes of summarizing the disclosure, certain aspects, advantages and novel features of the inventions have been described herein. It is to be understood that not necessarily all such advantages can be achieved in accordance with any particular embodiment of the inventions disclosed herein. Thus, the inventions disclosed herein can be embodied or carried out in a manner that achieves or optimizes one advantage or group of advantages as taught herein without necessarily achieving other advantages as can be taught or suggested herein.

BRIEF DESCRIPTION OF THE DRAWINGS

Throughout the drawings, reference numbers can be reused to indicate correspondence between referenced elements. The drawings are provided to illustrate embodiments of the inventions described herein and not to limit the scope thereof.

DETAILED DESCRIPTION

Figure 1:
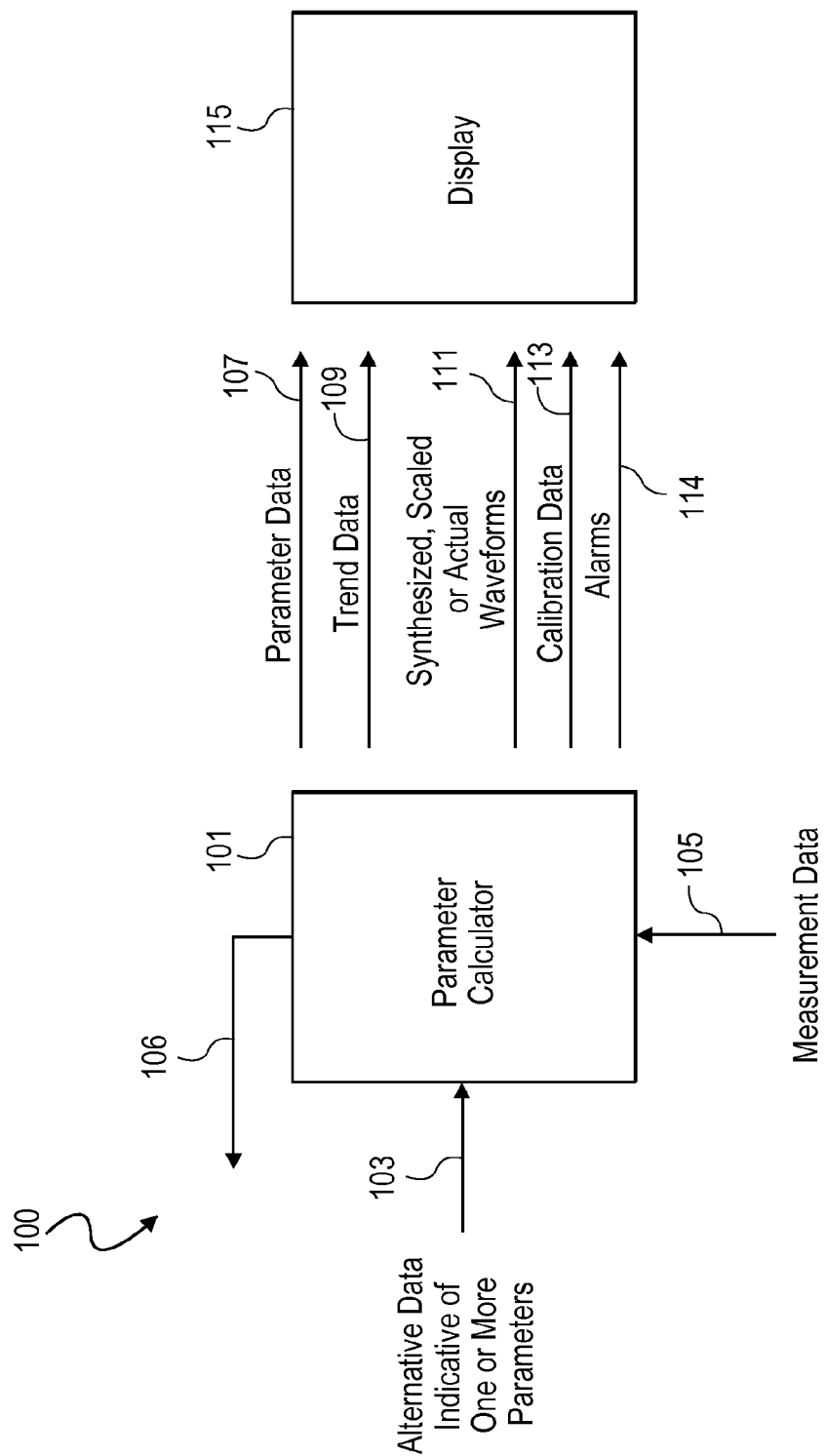
FIG. 1 illustrates an embodiment of a calibration system.

Noninvasive optical sensors can use spectrophotometry techniques to measure a variety of blood constituents, including for example, glucose, oxygen saturation, hemoglobin, methemoglobin, carboxyhemoglobin, other hemoglobin species, concentrations of the same, and the like. In addition, noninvasive optical sensors can also be used to measure a variety of other physiological parameters, including pulse rate, perfusion, and the like. An optical sensor can include one or more emitters that shine light through tissue of a living person, such as through a finger, toe, or foot. One or more detectors can receive the transmitted light after attenuation by the tissue and can generate one or more signals responsive to the attenuated light. A processor can process the one or more signals to derive measurements of one or more physiological parameters.

Noninvasive optical sensors can be calibrated empirically by obtaining measurements from a population of users. By comparing the noninvasive measurements with measurements of known parameter values in the population, a calibration curve can be generated. Because this initial calibration curve may be generated based on a population of individuals, it may not accurately reflect parameter levels for certain individuals. The optimal calibration curve for one individual can differ from the initial curve because of skin variations resulting from pigmentation, UV damage, age, erythema, or the like. Different calibration curves can also result from fingernail variations and variations in individuals' hemoglobin species.

This disclosure describes, among other features, systems and methods for customizing calibration curves, parameter algorithms, and the like to individual users. In certain embodiments, an initial calibration curve generated based on a population can be used as a starting point in an algorithm for measuring a physiological parameter such as glucose. The measurement algorithm can determine one or more initial measurement values for a user based on the initial calibration curve. In certain embodiments, one or more alternative measurements, such as invasive or minimally invasive measurements, can periodically or sporadically be input into the measurement algorithm. The algorithm can use the alternative measurements to adapt the calibration curve to the individual. As a result, measurements for the individual can more accurately reflect the individual's actual parameter values.

In the example context of glucose, measurement information from a finger-prick glucose meter or from another glucose sensor can be supplied to a noninvasive glucose device. For instance, a user could manually input a measurement obtained from a finger prick glucose meter into the noninvasive glucose device, or the noninvasive device might have a built-in finger prick meter. An adaptive glucose algorithm in the noninvasive device can adaptively recalibrate itself based on measurements received from the finger prick meter. In other embodiments, noninvasive parameter measurements can be used to calibrate or adjust invasive or minimally-invasive measurements.

For purposes of illustration, the remainder of this disclosure is described primarily in the context of glucose. However, the features described herein can be applied to other blood constituents or concentrations thereof and to other physiological parameters.

FIG. 1 illustrates an embodiment of a calibration system 100 that can adaptively adjust parameter measurements of a user. The calibration system 100 can start with an empirically-derived model for measuring one or more parameters. The empirical model can be a calibration curve that is generated based on measurement data taken from a population. Advantageously, in certain embodiments, the calibration system 100 can adapt the empirical model to an individual. As a result, measurements taken for the individual can be more accurate.

In the depicted embodiment, the calibration system 100 includes a parameter calculator 101. The parameter calculator 101 can include hardware (such as one or more processors), software, and/or firmware for calculating a physiological parameter such as glucose, oxygen saturation, hemoglobin, or the like. Inputs to the parameter calculator 101 can include, among others, measurement data 105 and alternative data 103 indicative of one or more parameters. The measurement data 105 can be obtained from a physiological sensor (not shown), such as a noninvasive optical sensor. Examples of noninvasive optical sensors are described below (see, e.g., FIGS. 4 and 12).

The alternative data 103 can be obtained from an alternative source, such as another patient monitor or another sensor (not shown). The alternative patient monitor can be an invasive or minimally-invasive monitor or can even be another noninvasive monitor. For example, in the context of glucose, the alternative patient monitor could be a spot-check monitor (e.g., a finger-prick glucose meter) or a continuous glucose monitor.

The parameter calculator 101 can calculate one or more physiological parameters based on the measurement data 105. If the measurement data 105 is provided by an optical sensor, the measurement data 105 can include light transmittance values after attenuation by tissue of a patient. The parameter calculator 101 can compare the transmittance values or a ratio derived from the transmittance values to a calibration curve to obtain a parameter value.

As an example, a pulse oximetry sensor can shine red and infrared wavelengths of light into a tissue site. A photodetector can receive the red and infrared light attenuated by the tissue site, and in response, transmit a measurement data 105 signal to the parameter calculator 101. The parameter calculator 101 can compute a ratio of the red to infrared values in the measurement data 105 and compare this ratio with an empirically-generated calibration curve to obtain a value for oxygen saturation ($SpO_2$).

In certain embodiments, the parameter calculator 101 advantageously uses the alternative data 103 to adjust calculation of the one or more physiological parameters. For instance, the parameter calculator 101 can use the alternative data 105 to adjust an algorithm for calculating a physiological parameter. In one embodiment, adjusting the algorithm can include adjusting an empirically-derived calibration curve used by the algorithm. Advantageously, in certain embodiments, the calibration curve used by the parameter calculator 101 can therefore account for characteristics of an individual under measurement. Embodiments of algorithms that can be used by the parameter calculator 101 are described in greater detail below with respect to FIGS. 5 through 11B.

The parameter calculator 101 can output parameter data 107 indicative of the calculated parameters. The parameter data 107 can be displayed on a display device 115. The parameter calculator 101 could also output the alternative data 103. For example, the parameter calculator 101 could output a finger-prick glucose measurement alongside or in place of a noninvasive glucose measurement. In another embodiment, the parameter calculator 101 provides parameter values as an output 106 to another device, for example, over a network.

The parameter calculator 101 can also calculate trend data reflecting trend information for the parameter data 107. The parameter calculator 101 can also synthesize or scale waveform data. In addition to outputting the parameter data 107, the parameter calculator 101 can output trend data 109, synthesized, scaled, or actual waveforms 111, calibration data 113, and alarms 114. The calibration data 113 can include information related to calibrations performed by the parameter calculator 101 (see, e.g., FIG. 7). The parameter calculator 101 can provide the outputs 107, 109, 111, 113 to the display 115, to a separate patient monitoring device, or to another device configured to receive physiological parameter information.

In an embodiment, the parameter calculator 101 is implemented in a single monitoring device. In an embodiment, the features of the parameter calculator 101 are distributed among separate devices. In an embodiment, the parameter calculator 101 includes a processor, processor board, or an Original Equipment Manufacture (OEM) board. In an embodiment, the parameter calculator 101 is portable. Data communicated between the various components of the calibration system 100 can be communicated through cables or wirelessly. Other inputs and/or outputs can be included with the system. For example, an error data output can be used to communicate an error calculated between the measured data 105 and the alternative data 103.

Figure 2:
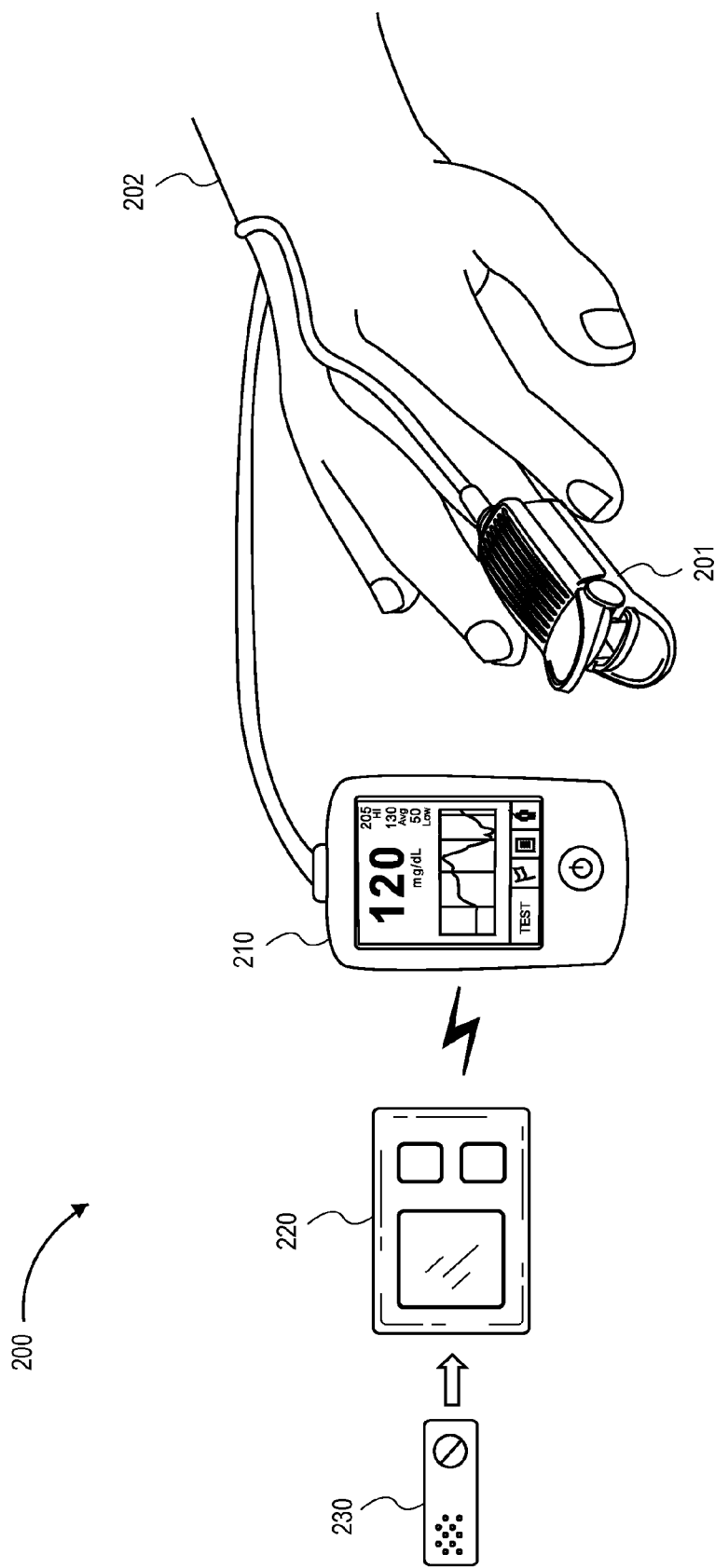
FIG. 2 illustrates an embodiment of a monitoring system that can implement the calibration system FIG. 1.

FIG. 2 illustrates an example monitoring system 200 that can implement the calibration system 100 of FIG. 1. The monitoring system 200 includes a noninvasive monitor 210, which is coupled to an individual 202 via a sensor 201. The sensor 201 is an example of a noninvasive optical sensor. The sensor 201 can provide measurement data to the noninvasive monitor 210, which can calculate a physiological parameter based at least in part on the measurement data and display the physiological parameter. The noninvasive monitor 210 can output glucose values derived from the sensor 210. The noninvasive monitor 210 can measure glucose values continuously or can be used for spot-checks.

The noninvasive monitor 210 can implement the calibration system 100 described above. For example, the noninvasive monitor 210 can adjust a glucose algorithm based on alternative data received from an alternative monitor. The alternative monitor in the depicted embodiment is a glucose meter 220, sometimes referred to as a glucometer or a finger-prick meter. The individual 202 can use the glucose meter 220 to prick the individual's finger. The individual can then apply a blood sample to a test strip 230. The individual can insert the test strip 230 into the glucose monitor 220, which can determine a glucose measurement from the blood sample on the test strip 230.

The glucose meter 220 can provide glucose measurements to the noninvasive monitor 210 wirelessly or through a wired connection. Alternatively, the individual 202 can input measurement values calculated by the glucose meter 220 into the noninvasive monitor 210. The noninvasive monitor 210 can then use the features of the calibration system 100 described above and in greater detail below to adjust the calculation of noninvasive glucose.

Figure 3:
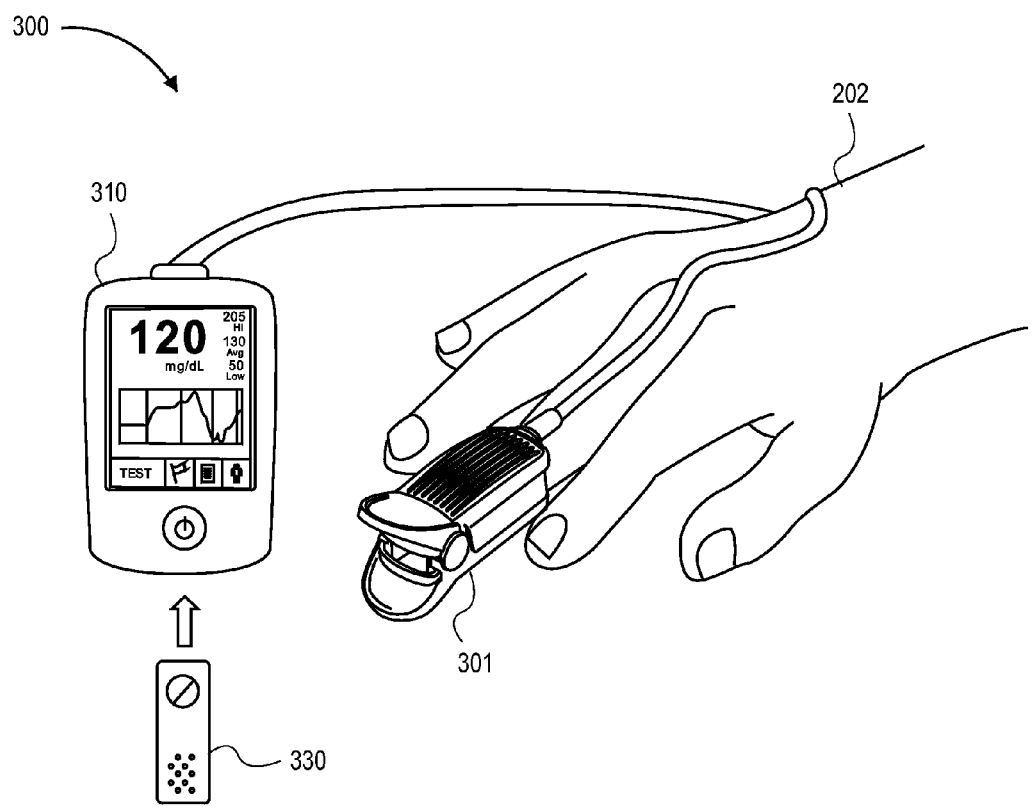
FIG. 3 illustrates another embodiment of a monitoring system that can implement the calibration system FIG. 1.

FIG. 3 illustrates another example monitoring system 300 that can implement the calibration system 100 of FIG. 1. The monitoring system 300 includes a monitor 310, which like the noninvasive monitor 210, obtains glucose measurements noninvasively from a sensor 301 coupled to an individual 202. Additionally, the monitor 300 includes the functionality of the glucose meter 220 described above. Namely, the monitor 300 can be used to obtain blood samples from a test strip 330. Thus, in certain embodiments, the monitor 310 can calculate both noninvasive glucose values and alternative glucose values. The monitor 310 can implement the calibration system 100 of FIG. 1 to adjust calculation of the noninvasive glucose based at least in part on the alternative glucose measurements. Although not shown, in other embodiments the monitor 310 can include the features of a continuous minimally-invasive glucose monitor instead of or in addition to the features of a finger-prick monitor.

Figure 4:
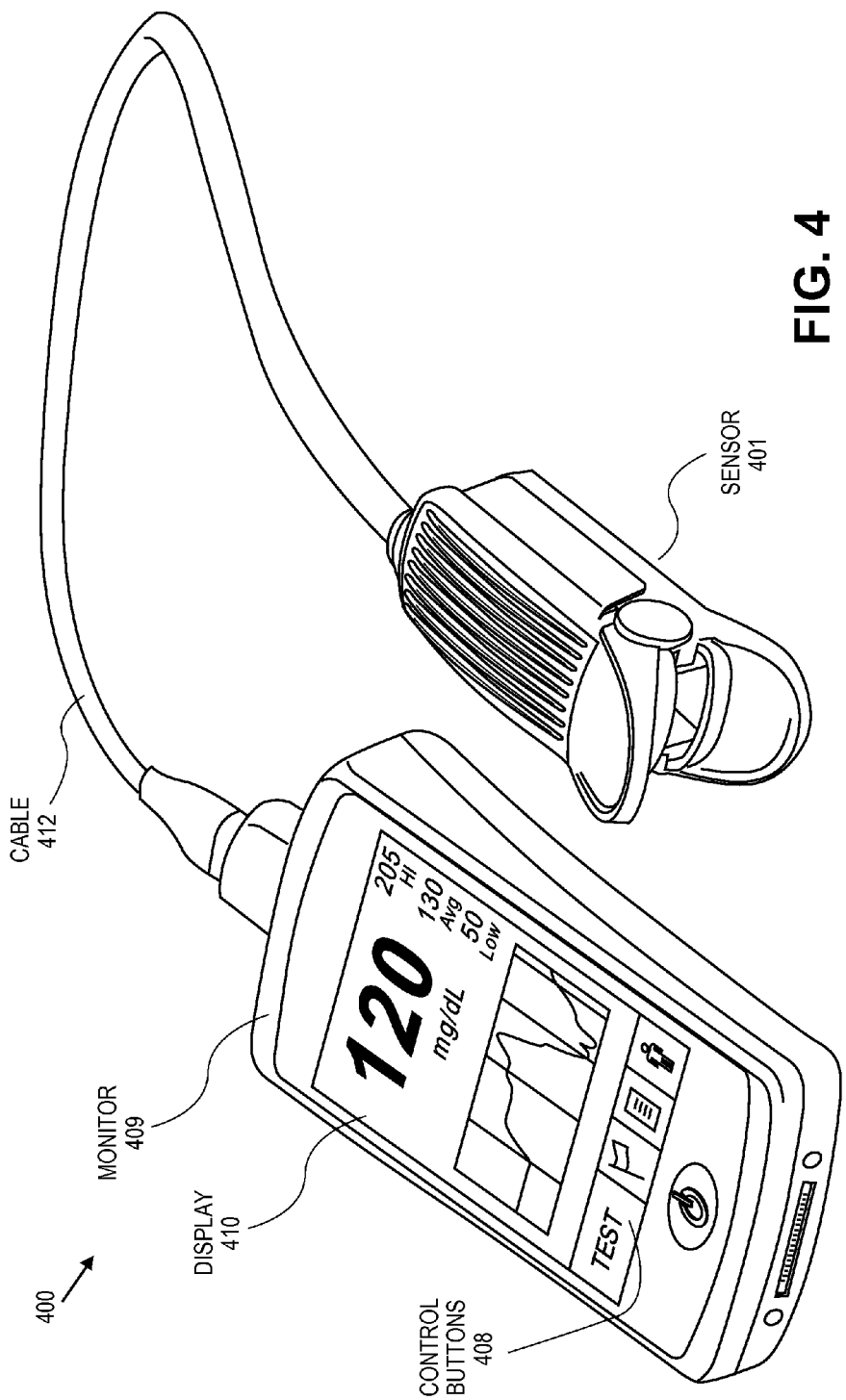
FIG. 4 illustrates an embodiment of a physiological monitor that may be used in the monitoring systems of FIG. 2 or 3.

FIG. 4 illustrates another example monitoring device 400 in which the calibration system 100 can be housed. Advantageously, in certain embodiments, the example monitoring device 400 shown can have a shape and size that allows a user to operate it with a single hand or attach it, for example, to a user's body or limb.

In the depicted embodiment, the monitoring device 400 includes a finger clip sensor 401 connected to a monitor 409 via a cable 412. In the embodiment shown, the monitor 409 includes a display 410, control buttons 408 and a power button. Moreover, the monitor 409 can advantageously include electronic processing, signal processing, and data storage devices capable of receiving signal data from the sensor 401, processing the signal data to determine one or more output measurement values indicative of one or more physiological parameters of a user, and displaying the measurement values, trends of the measurement values, combinations of measurement values, and the like.

The cable 412 connecting the sensor 401 and the monitor 409 can be implemented using one or more wires, optical fiber, flex circuits, or the like. In some embodiments, the cable 412 can employ twisted pairs of conductors in order to minimize or reduce cross-talk of data transmitted from the sensor 401 to the monitor 409. Various lengths of the cable 412 can be employed to allow for separation between the sensor 401 and the monitor 409. The cable 412 can be fitted with a connector (male or female) on either end of the cable 412 so that the sensor 401 and the monitor 409 can be connected and disconnected from each other. Alternatively, the sensor 401 and the monitor 409 can be coupled together via a wireless communication link, such as an infrared link, a radio frequency channel, or any other wireless communication protocol and channel. The sensor 401 could also be integrated with a monitor 409 in other embodiments.

Moreover, the sensor 401 and/or monitor 409 can include any of the features described in any of the following related applications, each of which is hereby incorporated by reference in its entirety: U.S. application Ser. No. 12/534,827, filed Aug. 3, 2009, titled "MULTI-STREAM DATA COLLECTION SYSTEM FOR NONINVASIVE MEASUREMENT OF BLOOD CONSTITUENTS"; U.S. application Ser. No. 12/534,812, filed Aug. 3, 2009, titled "MULTI-STREAM SENSOR FRONT ENDS FOR NONINVASIVE MEASUREMENT OF BLOOD CONSTITUENTS"; U.S. application Ser. No. 12/534,823, filed Aug. 3, 2009, titled "MULTI-STREAM SENSOR FOR NONINVASIVE MEASUREMENT OF BLOOD CONSTITUENTS"; U.S. application Ser. No. 12/534,825, filed Aug. 3, 2009, titled "MULTI-STREAM EMITTER FOR NONINVASIVE MEASUREMENT OF BLOOD CONSTITUENTS"; U.S. application Ser. No. 12/497,528, filed Jul. 2, 2009, titled "NOISE SHIELDING FOR A NONINVASIVE DEVICE"; U.S. application Ser. No. 12/497,523, filed Jul. 2, 2009, titled "CONTOURED PROTRUSION FOR IMPROVING SPECTROSCOPIC MEASUREMENT OF BLOOD CONSTITUENTS"; U.S. Provisional Application No. 61/239,741, filed Sep. 3, 2009, titled "EMITTER DRIVER FOR NONINVASIVE PATIENT MONITOR"; U.S. Design Application No. 29/323,409, filed Aug. 25, 2008, titled "PATIENT MONITORING SENSOR"; U.S. Design Application No. 29/323, 408, filed Aug. 25, 2008, titled "PATIENT MONITOR"; U.S. application Ser. No. 12/497,506, filed Jul. 2, 2009, titled "HEAT SINK FOR NONINVASIVE MEDICAL SENSOR"; U.S. Provisional Application No. 61/243,507, filed Sep. 17, 2009, titled "IMPROVING ANALYTE MONITORING USING ONE OR MORE ACCELEROMETERS"; U.S. Provisional Application No. 61/177,971, filed May 13, 2009, titled "CALIBRATIONLESS SPECTROPHOTOMETER"; and U.S. Provisional Application No. 61/228,495, filed Jul. 24, 2009, titled "INTERFERENCE DETECTOR FOR PATIENT MONITOR."

The monitor 409 can be attached to the patient. For example, the monitor 409 can include a belt clip or straps (not shown) that facilitate attachment to a patient's belt, arm, leg, or the like. The monitor 409 can also include a fitting, slot, magnet, LEMO snap-click connector, or other connecting mechanism to allow the cable 412 and sensor 401 to be attached to the monitor 409.

The monitor 409 can also include other components, such as a speaker, power button, removable storage or memory (e.g., a flash card slot), an AC power port, and one or more network interfaces, such as a universal serial bus interface or an Ethernet port. For example, the monitor 409 can include a display 410 that can indicate a measurement for glucose, for example, in mg/dL. Other analytes and forms of display can also appear on the monitor 409.

The sensor 401 can measure various blood constituents or analytes noninvasively using multi-stream spectroscopy. In an embodiment, the multi-stream spectroscopy can employ visible, infrared and near infrared wavelengths. The sensor 401 can include photocommunicative components, such as an emitter, a detector, and other components (not shown). The emitter can include a plurality of sets of optical sources that, in an embodiment, are arranged together as a point source. The various optical sources can emit a sequence of optical radiation pulses at different wavelengths towards a measurement site, such as a patient's finger. Detectors can then detect optical radiation from the measurement site. The optical sources and optical radiation detectors can operate at any appropriate wavelength, including, for example, infrared, near infrared, visible light, and ultraviolet. In addition, the optical sources and optical radiation detectors can operate at any appropriate wavelength, and modifications to the embodiments desirable to operate at any such wavelength can be used in certain embodiments. The sensor 401 or the monitor 409 can also provide outputs to a storage device or network interface.

In addition, although a single sensor 401 with a single monitor 409 is shown, different combinations of sensors and device pairings can be implemented. For example, multiple sensors can be provided for a plurality of differing patient types or measurement sites or even patient fingers. As described above with respect to FIG. 3, the monitor 409 can also include noninvasive or minimally-invasive features for measuring analytes such as glucose.

Figure 5A:
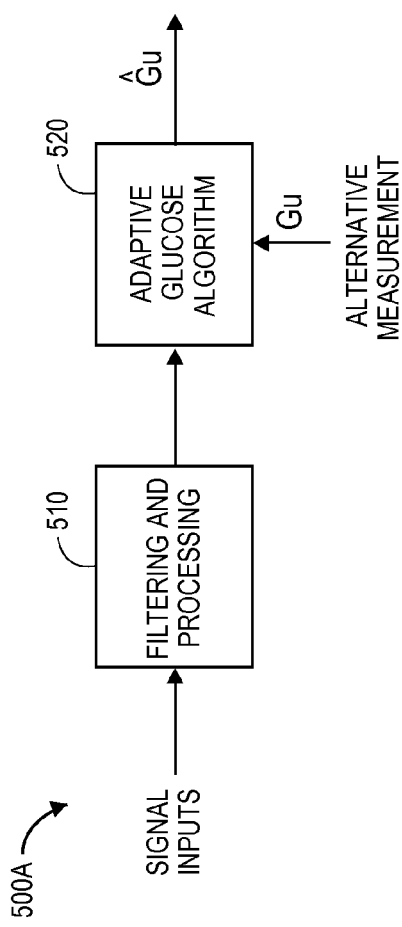
FIGS. 5A through 5C illustrate embodiments of glucose monitoring systems.
Figure 5B:
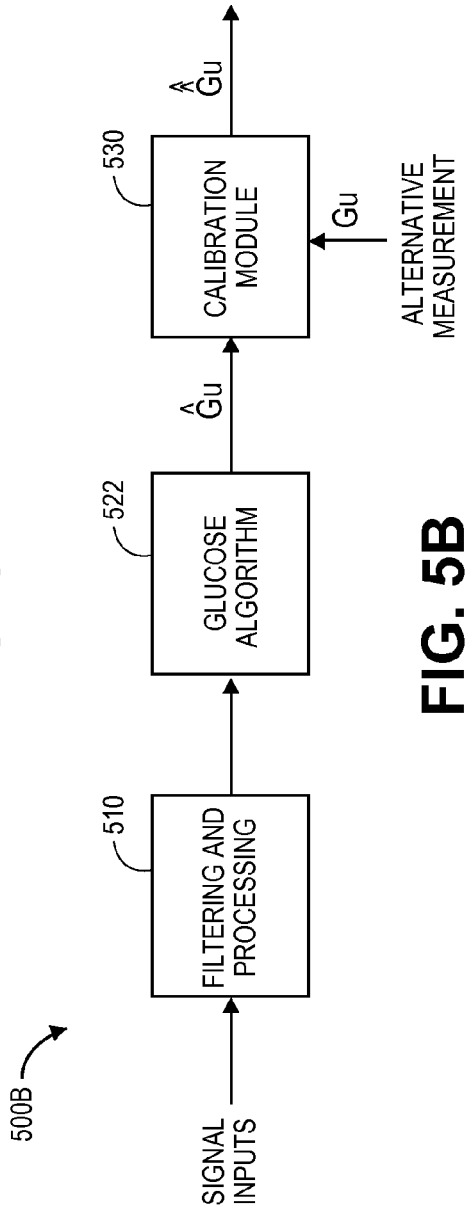
Figure 5C:
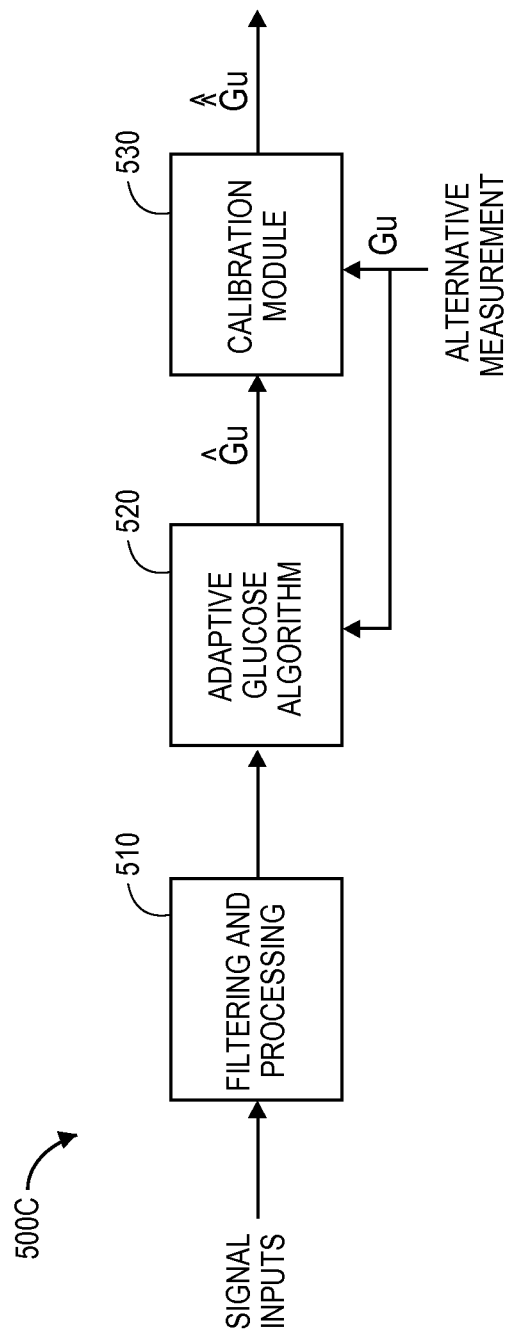

FIGS. 5A through 5C illustrate embodiments of glucose monitoring systems 500. Each of the glucose monitoring systems 500 can implement certain features of the parameter calculator 101 described above.

Referring to FIG. 5A, an embodiment of a glucose monitoring system 500A is shown. In the glucose monitoring system 500A, signal inputs are provided to a filtering and processing module 510. The signal inputs can include signals received from a noninvasive optical sensor or the like. For example, the signal inputs could include optical signals, photoplethysmograph signals, transmittance signals, combinations of the same, and the like. Moreover, in some implementations, the input signals can include data regarding optical path length between one or more emitters and one or more detectors, a straight line distance between an emitter and a detector, and an angle between the straight line distance and an axis parallel to or substantially parallel to a detector shell or finger.

The filtering and processing module 510 can include analog and/or digital circuitry for filtering and processing one or more of the signal inputs. For instance, the module 510 can include analog conditioning circuitry, anti-alias filters, analog-to digital-converters, and the like. The module 510 can pride one or more outputs to an adaptive glucose algorithm 520. These outputs can include one or more ratios of wavelengths of light, transmittance values, coefficients of absorption, absorption values, combinations of the same, and the like.

The adaptive glucose algorithm 520 can receive these outputs as well as an alternative measurement input, $G_u$. The adaptive glucose algorithm 520 can be implemented in hardware and/or software. The alternative measurement $G_u$ can be an invasive or minimally-invasive glucose value. In another embodiment, the alternative measurement input can include raw signal inputs from an invasive or minimally-invasive glucose monitor.

In certain embodiments, the adaptive glucose algorithm 520 initially starts noninvasive monitoring using an empirically-derived calibration curve. The adaptive glucose algorithm 520 can then use the alternative measurement to adjust the calibration curve to better match characteristics of a user. The adaptive glucose algorithm 520 can output a noninvasive measurement $\hat{G}_u$, which reflects adjustment by the alternative measurement $G_u$. More detailed embodiments of the adaptive glucose algorithm 520 are described below with respect to FIG. 6.

FIG. 5B illustrates another embodiment of a glucose monitoring system 500B. The system 500B also includes the filtering and processing module 510, which receives the signal inputs and provides filtered and processed outputs to a glucose algorithm 522. The glucose algorithm 522 in the depicted embodiment uses an empirically-derived calibration curve to generate noninvasive glucose measurements $\hat{G}_u$. The measurements $\hat{G}_u$ are output to a calibration module 530.

The calibration module 530 can be implemented in hardware and/or software. The calibration module 530 can calibrate the noninvasive glucose measurements $\hat{G}_u$ using one or more alternative glucose measurements $G_u$. For example, the calibration module 530 could perform regression or another statistical estimation technique to calibrate the noninvasive measurement. The glucose monitoring system 500B can therefore calibrate glucose measurements based on alternative measurements without adapting the glucose algorithm 522.

Examples of these calibration techniques are described below with respect to FIG. 7. Additional calibration embodiments that might be performed by the calibration module are described below with respect to FIGS. 10 and 11.

FIG. 5C illustrates another embodiment of a glucose monitoring system 500C. The system 500C includes the features of both the glucose monitoring systems 500A and 500B described above. For example, signal inputs are provided to a filtering and processing block 510, which provides outputs to the adaptive glucose algorithm 520. The adaptive glucose algorithm 520 can receive an alternative glucose measurement $G_u$ and use this measurement to adjust the calibration curve. The adaptive glucose algorithm 520 can output a noninvasive measurement $\hat{G}_u$, which can reflect adjustment by the alternative measurement $G_u$.

The output $\hat{G}_u$ of the adaptive glucose algorithm 520 is provided to the calibration module 530, which can further calibrate the noninvasive glucose measurement $\hat{G}_u$ with the alternative measurement $G_u$. The resulting output of the calibration module 530 is a calibrated glucose value $\hat{G}_u$.

Figure 6:
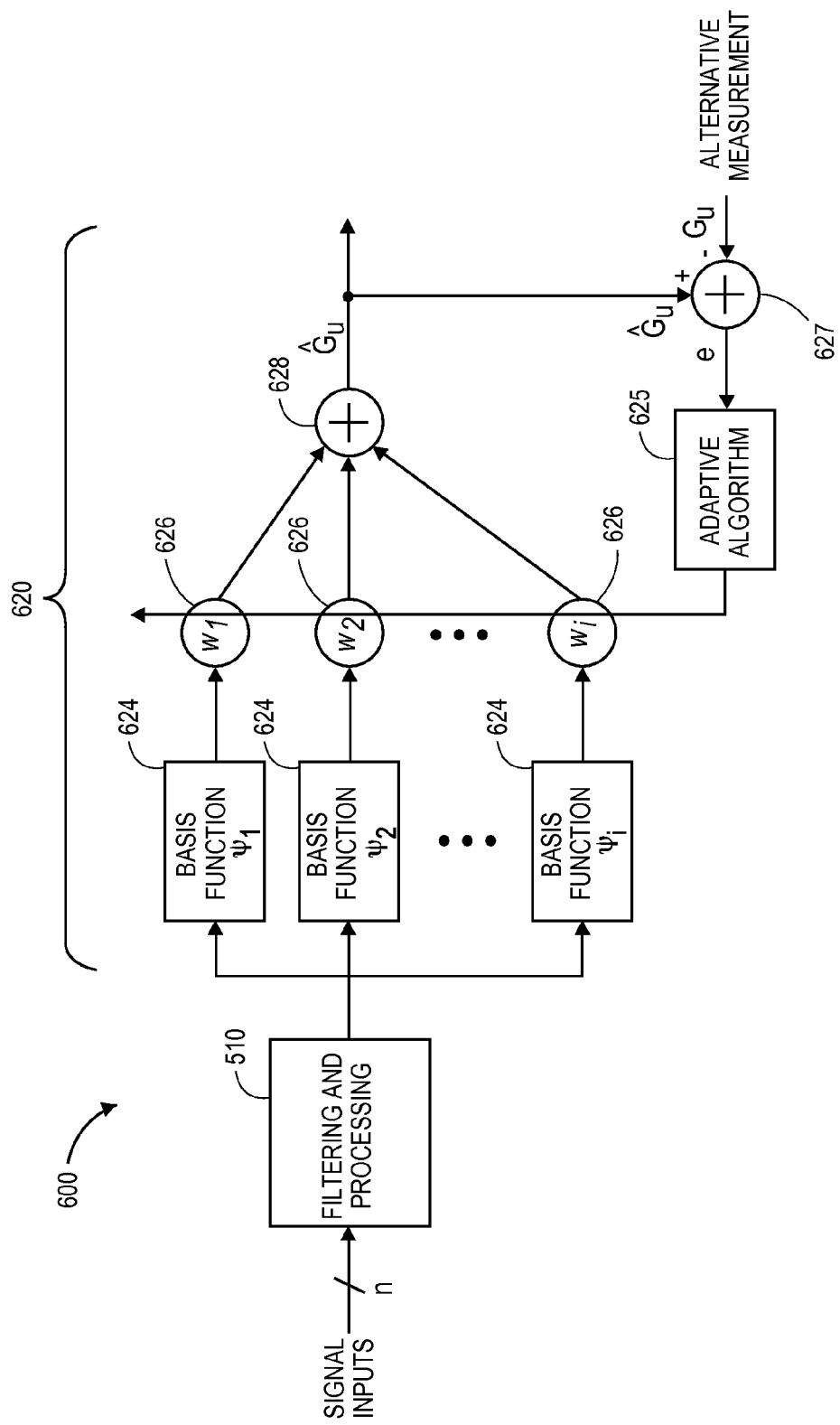
FIGS. 6 and 7 illustrate additional embodiments of glucose monitoring systems.

FIG. 6 illustrates a more detailed embodiment of a glucose monitoring system 600. In particular, the glucose monitoring system 600 is a more detailed embodiment of the glucose monitoring system 500A of FIG. 5A. As such, the glucose monitoring system 600 includes the filtering and processing module 510 and an adaptive glucose algorithm 620.

As before, signal inputs are received by the filtering and processing module 510, which outputs one or more ratios of wavelengths of light, transmittance values, coefficients of absorption, absorption values, and the like. In some embodiments, the noninvasive sensor used to obtain the signal inputs obtains n signals corresponding to n detected wavelengths of light, where n is an integer. The filtering and processing module 510 can output ratios of a subset of these wavelengths. For two wavelengths, the module 510 could output a single ratio. For multiple (e.g., more than two) wavelengths, the module 510 could combine any of the wavelengths into ratios.

The adaptive glucose algorithm 620 receives the ratios from the module 510 and processes the ratios or other outputs to determine an initial noninvasive glucose measurement $\hat{G}_u$. In the depicted embodiment, the adaptive glucose algorithm 620 includes a plurality of basis functions 624 ($\psi_i$). Each of the basis functions 624 can receive one or more ratios (or other outputs of the filtering and processing module 510) as inputs. The basis functions 624 can be blending functions or the like. The basis functions 624 are multiplied by weights 626 ($w_i$) to produce a noninvasive glucose measurement $\hat{GG}_u$. The combination of basis functions 624 and weights 626 can be expressed as follows, via sum block 628:

$$\hat{G}_u = \sum_i w_i \psi_i \quad (1)$$

In one embodiment, the basis functions 624 are polynomial functions, such as x, $x^2$, $(x_1+x_2)/2$, and the like, where x represents a ratio or some other output of the filtering and processing module 510. The basis functions 624 can also be logarithmic (e.g., ln(x)), trigonometric, Fourier basis functions, wavelet basis functions, combinations of the same, and the like. In another embodiment, at least some of the basis functions 624 are radial basis functions. The radial basis functions are Gaussian in one embodiment, having the form $$\phi(r) = e^{-\alpha(r-r_0)^T(r-r_0)} \quad (2)$$

where r represents a vector of ratios, $r_0$ represents an initial vector of ratios, and $\alpha$ is a constant.

In certain embodiments, the combination of the basis functions 624 and weights 626 approximates a calibration curve. Application of the basis functions 624 and weights 626 to the ratios (or other module 510 outputs) effectively applies the calibration curve to the ratios (or other outputs). Advantageously, in some implementations, radial basis functions 624 can approximate the calibration curve more accurately than other bases, such as polynomial bases.

In one embodiment, the basis functions 624 and weights 626 are selected empirically. In addition, the number of basis functions 624 and weights 626 used can be determined empirically. In one embodiment, the more ratios that are provided as inputs to the adaptive glucose algorithm 620, the fewer basis functions 624 and weights 626 that might be used, and vice versa.

Because the basis functions 624 and weights 626 are selected empirically, they may not accurately represent a true calibration curve for a given individual. Thus, in certain embodiments, an adaptive algorithm 625 can be used to adapt the weights 626 of the glucose algorithm 620. The adaptive algorithm 625 receives an error signal or cost function e(n), which can be the difference between the noninvasive measurement $\hat{G}_u$ and an alternative (e.g., invasive) measurement $G_u$ (via sum block 627). In one embodiment, the adaptive algorithm 625 can minimize the cost function e(n) to obtain adjustment factors for the weights 626 or new weights 626.

Any of a variety of adaptive algorithms 625 may be used. For instance, the adaptive algorithm 625 could implement one or more of the following: a least mean squares algorithm (LMS), a least squares algorithm, a recursive least squares (RLS) algorithm, a Kalman filter, a joint process estimator, an adaptive joint process estimator, a least-squares lattice joint process estimator, a least-squares lattice predictor, a correlation canceller, optimized or frequency domain implementations of any of the above, any other linear predictor, combinations of the same, and the like.

The adaptive glucose algorithm 620 can adapt in other ways. For example, the adaptive glucose algorithm 620 could use fewer, more, or different types of basis functions 624 for certain individuals to adapt the calibration curve. In addition, in alternative embodiments, the adaptive glucose algorithm 620 adapts the raw signal output from the filtering and processing module 510 with the alternative measurement or a raw alternative measurement. For instance, in the monitoring system 300 of FIG. 3, where the monitor 310 includes noninvasive and minimally-invasive features together, the monitor 310 could adapt raw noninvasive signals with raw minimally-invasive signals.

Figure 7:
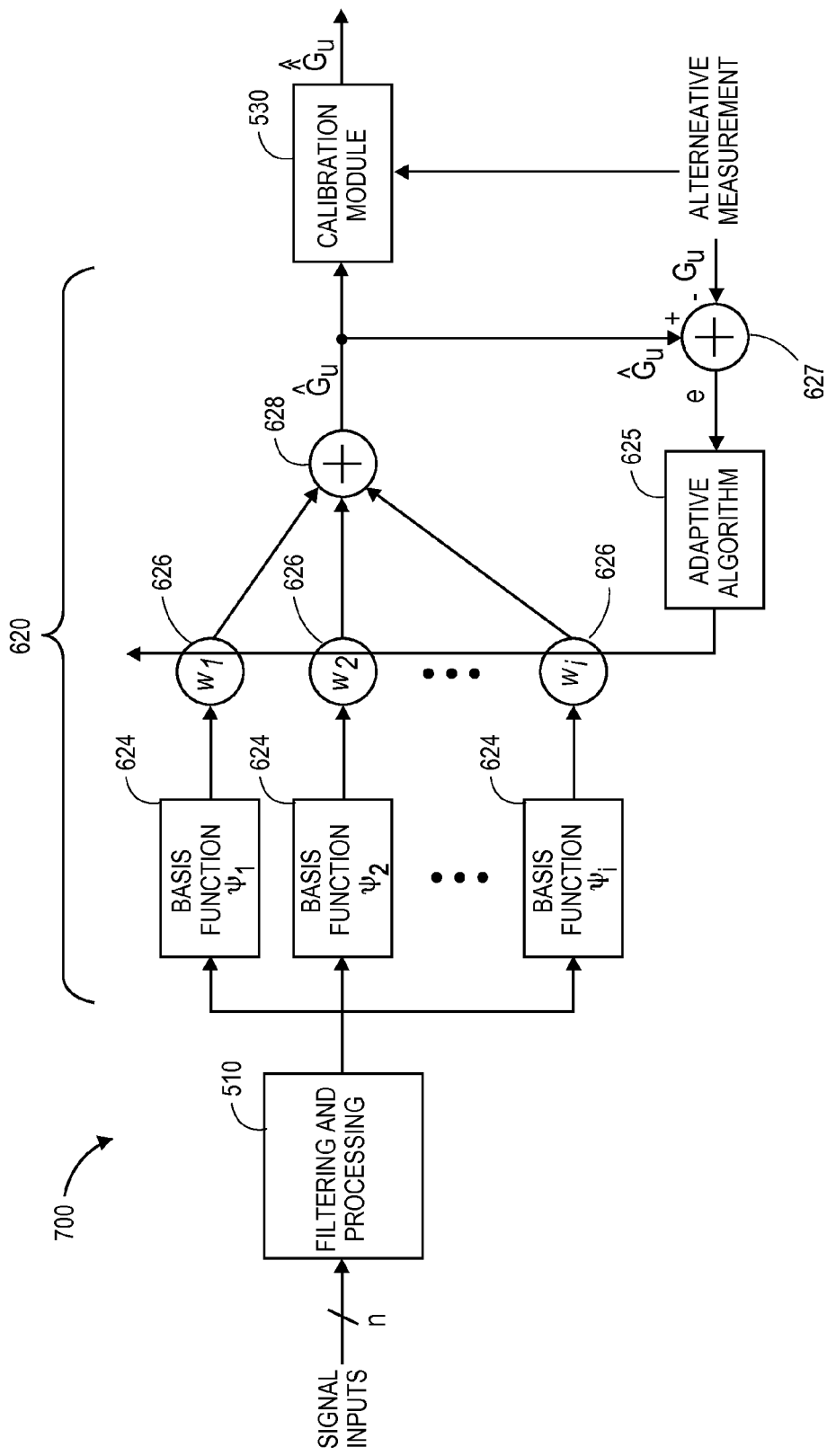

FIG. 7 illustrates another embodiment of a glucose monitoring system 700. The glucose monitoring system 700 includes the features of the glucose monitoring system 600. In addition, the glucose monitoring system 700 supplies the noninvasive output $\hat{G}_u$ to the calibration module 530 described above with respect to FIG. 5B. The calibration module 530 also receives an alternative measurement, for example, from an invasive or minimally-invasive monitor. The calibration module 530 can advantageously further refine the noninvasive measurement to output a calibrated glucose value $\hat{G}_u$.

The calibration module 530 can perform calibration using various techniques, such as linear regression. In one embodiment, the regression can be performed by first determining an offset, for example, as follows:

$$\text{offset} = G_u - \hat{G}_u \quad (3)$$

where $G_u$ represents an alternative glucose measurement and where $\hat{G}_u$ represents a noninvasive glucose measurement. The offset can be used to obtain a calibrated measurement, for example, as follows:

$$\hat{G}_u = \hat{G}_u + \text{offset} \quad (4)$$

where $\hat{GG}_u$ is the calibrated glucose value. Equation (4) can be refined in one embodiment by applying a multiplier to the noninvasive measurement. Equation (5) illustrates an example of using a multiplier:

$$\hat{G}u = \alpha \hat{G}_u + \text{offset} \quad (5)$$

where $\alpha$ is the multiplier.

In addition, multiple alternative and noninvasive measurements can be combined together in a system of linear equations based on equation (5) to calculate or estimate $\alpha$ and the offset values. An example of a system of two equations is shown in equation (6):

$$\begin{bmatrix} G_{u1} \\ G_{u2} \end{bmatrix} = \underbrace{\begin{bmatrix} \hat{G}_{u1} & 1 \\ \hat{G}_{u2} & 1 \end{bmatrix}}_{A} \begin{bmatrix} \alpha \\ \text{offset} \end{bmatrix} \quad (6)$$

In equation (6), A is a matrix. Assuming A is nonsingular, equation (6) can be solved for $\alpha$ and the offset as follows:

$$\begin{bmatrix} \alpha \\ \text{offset} \end{bmatrix} = A^{-1} \begin{bmatrix} G_{u1} \\ G_{u2} \end{bmatrix} \quad (7)$$

If A is singular, or if more than two alternative measurements are being analyzed, in some embodiments the pseudoinverse of A can be used to calculate α and the offset. For example:

$$\begin{bmatrix} \alpha \\ \text{offset} \end{bmatrix} = P_{INV}(A^{-1}) \begin{bmatrix} G_{u1} \\ G_{u2} \\ \vdots \\ G_{uN} \end{bmatrix} \quad (8)$$

where $P_{INV}(\ )$ denotes the Moore-Penrose pseudoinverse (or another suitable pseudoinverse).

In still other embodiments, polynomial regression may be used to calibrate the glucose measurements. Polynomial regression can take the form of a polynomial equation in $\hat{G}_u$ (a noninvasive measurement). One example of a polynomial function that may be used is shown in equation (9):

$$\hat{G}_u = P(\hat{G}_u) = \alpha_n \hat{G}_u^n + \alpha_{n-1} \hat{G}_u^{n-1} + \ldots + \text{offset} \quad (9)$$

where $P(\ )$ represents a polynomial operator, $\alpha_n$ represent the coefficients of the noninvasive measurement, and n is an integer that represents the order of the polynomial.

To solve for the coefficients $\alpha_n$ and the offset, a system of polynomial equations can be generated from multiple noninvasive and alternative measurements. This system can be written in matrix form as follows:

$$\underbrace{\begin{bmatrix} G_{u1} \\ G_{u2} \\ \vdots \\ G_{un+1} \end{bmatrix}}_{y} = \underbrace{\begin{bmatrix} \hat{G}_{u1}^n & \hat{G}_{u1}^{n-1} & \ldots & \hat{G}_{u1} \\ \hat{G}_{u2}^n & \hat{G}_{u2}^{n-1} & \ldots & \hat{G}_{u2} \\ \vdots & \vdots & \ddots & \vdots \\ \hat{G}_{un+1}^n & \hat{G}_{un+1}^{n-1} & \ldots & \hat{G}_{un+1} \end{bmatrix}}_{A} \underbrace{\begin{bmatrix} \alpha_n \\ \alpha_{n-1} \\ \vdots \\ \alpha_1 \\ \text{offset} \end{bmatrix}}_{x} \quad (10)$$

A solution to this system of equations can be found as follows:

$$x = A^{-1} y \quad (11)$$

Various estimation or approximation techniques could be used to avoid the computational inefficiency of calculating the inverse of A. In addition, other forms of regression or other approximation or estimation methods may be used to calibrate the noninvasive measurements.

Figure 8:
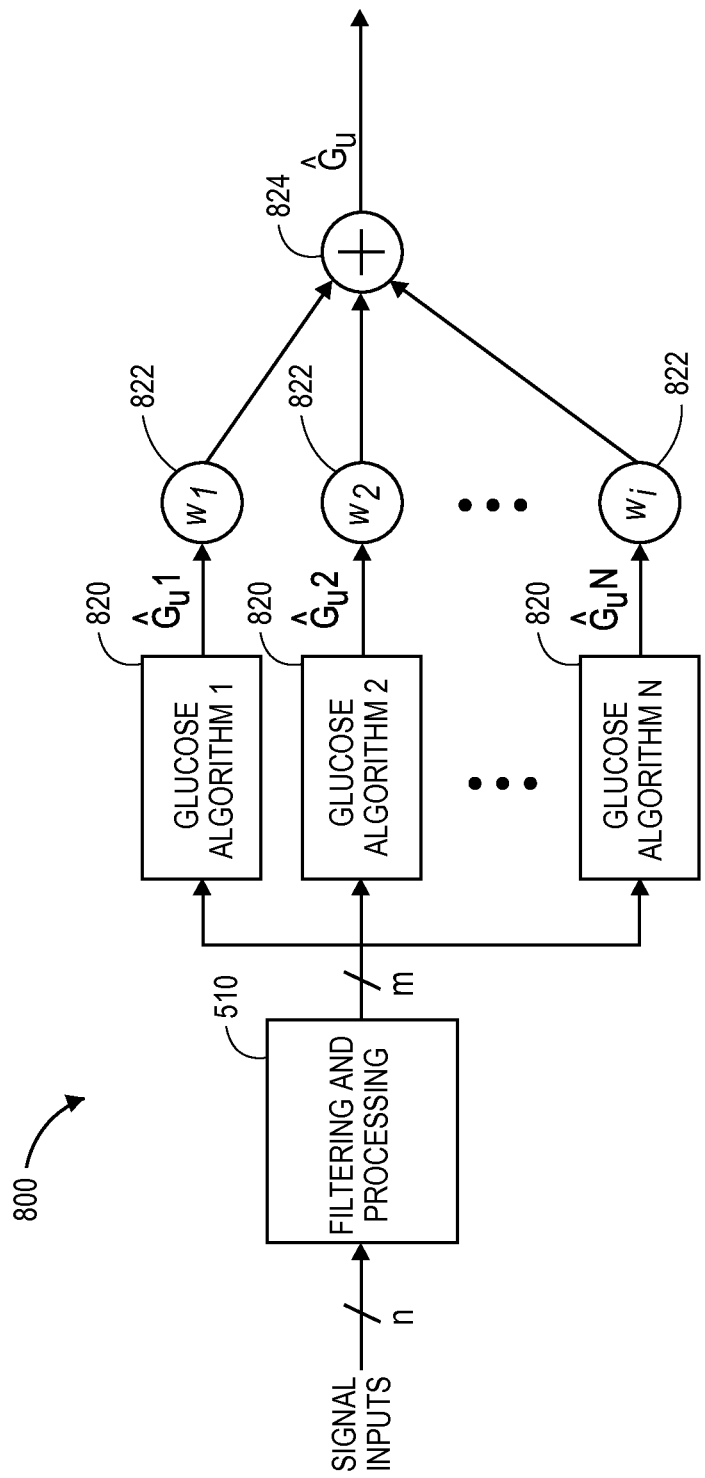
FIGS. 8 and 9 illustrate embodiments of parallel engines for glucose monitoring systems.
Figure 9:
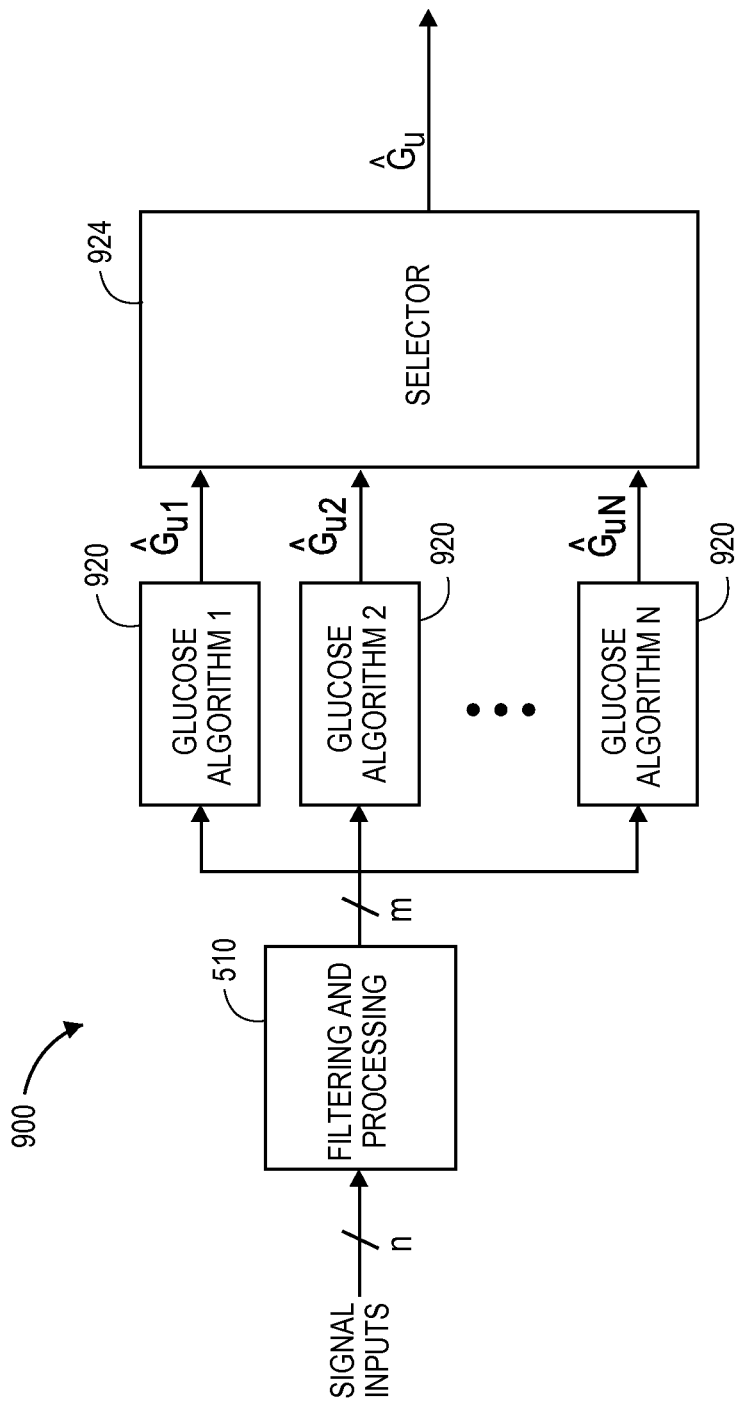

FIGS. 8 and 9 illustrate further embodiments of glucose monitoring systems 800, 900 that implement a plurality of glucose algorithms. Referring to FIGS. 8 and 9 together, signal inputs are received by the filtering and processing module 510, described above. The filtering and processing module 510 provides outputs, such as ratios or the like, to a plurality of glucose algorithms 820, 920. Each glucose algorithm outputs a glucose value $\hat{G}_{ui}$. The plurality of glucose algorithms 820, 920 can be considered parallel engines in certain embodiments.

Some or all of the glucose algorithms 820, 920 can be adaptive glucose algorithms, though this need not be the case. At least some of the algorithms 820, 920 can implement some or all of the features of the adaptive glucose algorithm 620 described above with respect to FIG. 6. Some of the glucose algorithms 820, 920 could use basis functions to approximate a calibration curve, for instance. Different ones of the algorithms 820, 920 could use different numbers or types of basis functions to provide different results. Advantageously, in certain embodiments, these results can be combined, compared, or otherwise selected to provide more accurate glucose values.

Referring to FIG. 8, weights 822 ($w_i$) can be applied to the glucose values from each algorithm and combined at a combiner 824 to output an overall glucose value $\hat{G}_u$. The weights 824 can average or otherwise blend the outputs of the glucose algorithms 820. Although not shown, these weights may be adapted using any of the adaptive algorithms described above, e.g., based on alternative measurements. Fewer than all of the algorithms may be combined in some embodiments; a subset of the algorithms 920 may be selected to be combined for certain individuals.

Referring to FIG. 9, the outputs of the algorithms 920 can be provided to a selector module 924, which can select one or more of the outputs of the algorithms 920 to output as a final glucose value $\hat{G}_u$. The selector 920 can select different algorithms 920 for different types of patients (e.g., neonates versus adults). Alternatively, the selector 920 can compare the outputs from the glucose algorithms 920 to determine which, if any, of the algorithms provided outliers. The selector 924 could reject the outliers and combine (e.g., average) the outputs of the remaining algorithms 920.

In yet another embodiment, the selector 924 could determine which of the algorithm outputs are close to each other (e.g., within a tolerance) and output a combination of those outputs 920. For example, if there are five algorithms 920 and three of the algorithms produce a similar output and two are outliers, the selector 924 could average the three similar outputs or select one of the three outputs as the final glucose value. Moreover, the selector 924 can learn over time and can select one or more algorithms 920 for a particular person based on past performance of that algorithm. Many other configurations and extensions of the selector 924 are possible.

Figure 10:
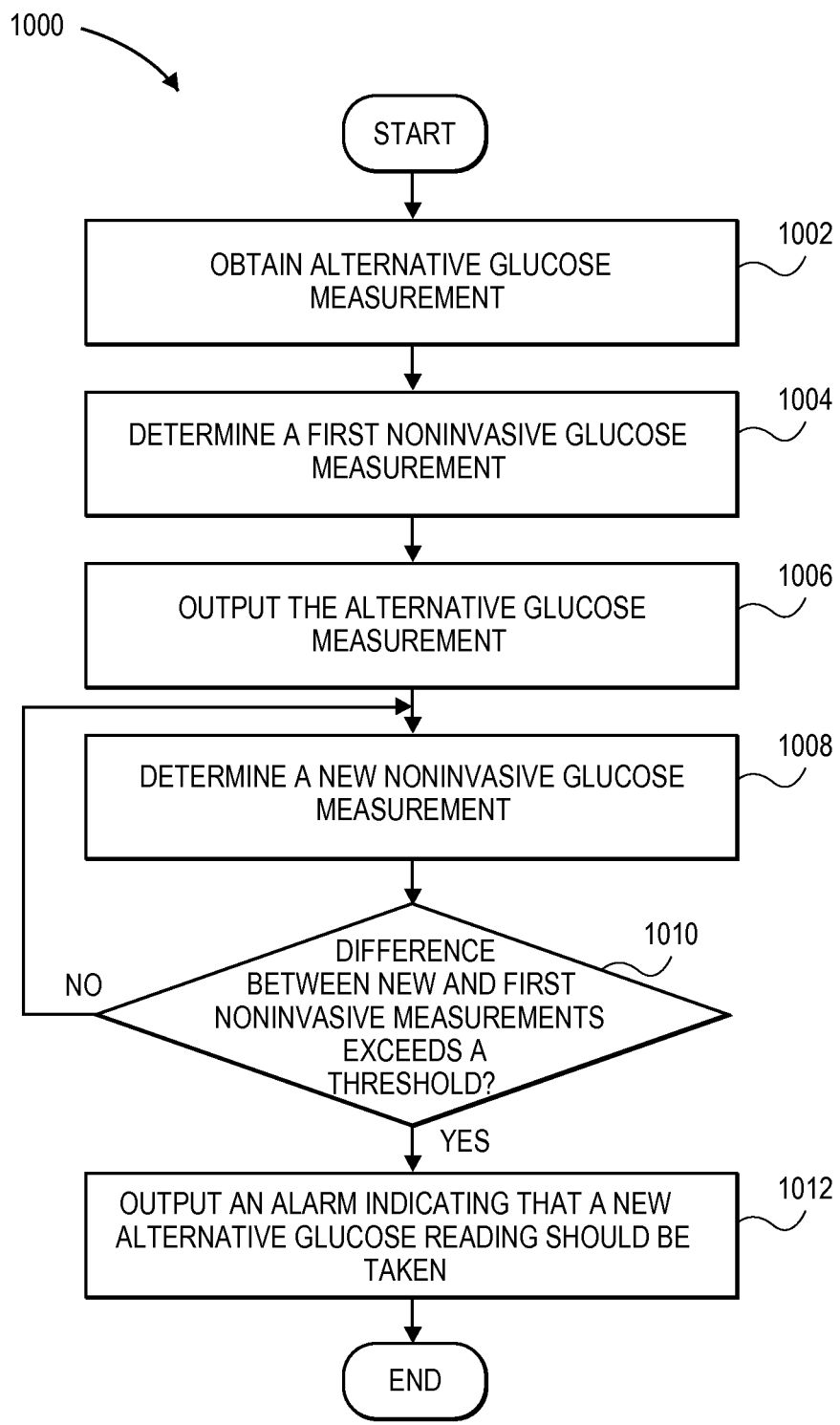
FIGS. 10 and 11A illustrate embodiments of processes for determining whether to suggest obtaining an alternative measurement of a physiological parameter.
Figure 11A:
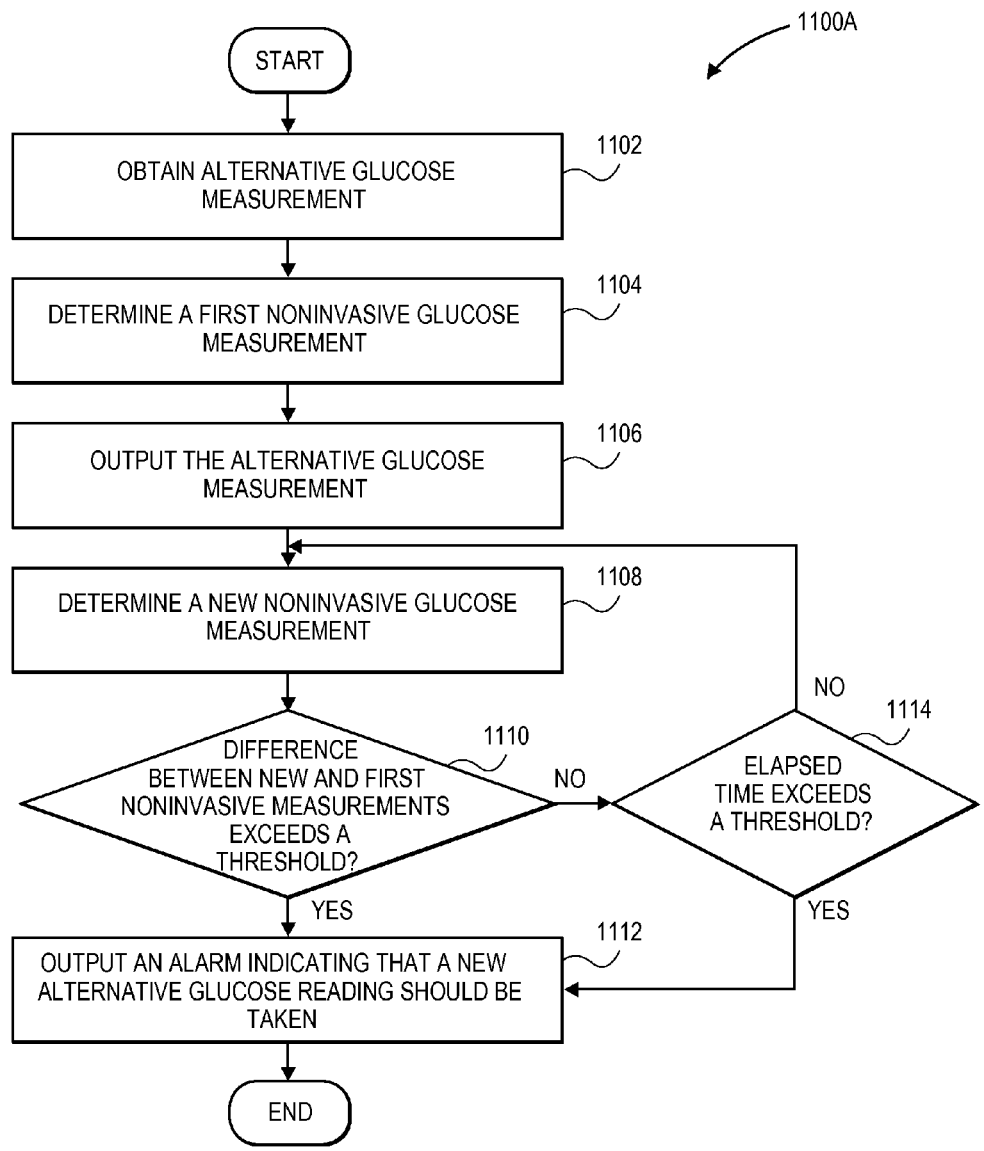

FIGS. 10 and 11A illustrate embodiments of processes 1000, 1100A for determining whether to suggest an alternative measurement of a physiological parameter. These processes can be implemented by the parameter calculator 101 or by any of the other systems described herein. Advantageously, the processes 1000, 1100A can receive alternative and noninvasive measurements as inputs. The processes 1000, 1100A can determine, based at least partly on the noninvasive measurements and/or based on an elapse of time, whether an alternative measurement should be taken. As a result, a user can be spared the discomfort of painful finger pricks or other invasive/minimally-invasive measurements while a noninvasive measurement is within a certain tolerance or while a certain amount of time has yet to elapse.

Referring to FIG. 10, at block 1002 of the process 1000, an alternative glucose measurement is obtained. The alternative glucose measurement can be obtained, for example, from an invasive or minimally-invasive device. At block 1004, a first noninvasive glucose measurement is determined. This block can be implemented by a noninvasive glucose device.

The alternative glucose measurement is output at block 1006, e.g., by the noninvasive device. Alternatively, the noninvasive glucose measurement can be output instead. At block 1008, a new noninvasive glucose measurement is determined. If at decision block 1010 a difference between the new and the first noninvasive measurements exceeds a threshold, an alarm or other indicator is output indicating or suggesting that a new alternative glucose measurement should be taken. Otherwise, the process 1000 loops back to block 1008, where a new noninvasive measurement is determined.

Thus, the process 1000 can loop from block 1010 to block 1008 until the noninvasive measurement changes enough to trigger an alarm or other indication. Advantageously, in certain embodiments, the process 1000 can therefore allow a user to postpone painful finger prick or other invasive tests, while the noninvasive measurement is within a certain tolerance of a finger-prick measurement.

In certain embodiments, the parameter calculator 101 of FIG. 1 performs the process 1000 by continuously comparing the noninvasive measurement to a stored alternative measurement or measurements. If the alternative measurements come from a continuous glucose or other monitor, the parameter calculator 101 can compare periodicity of the noninvasive and alternative measurements, peak value, low value, wave shape, or other factors. Additionally, in alternative embodiments, the parameter calculator 101 can output the noninvasive value instead of or in addition to the alternative value.

FIG. 11A illustrates another example process 1100A for determining whether to suggest an alternative measurement to be taken. As in the process 1000, alternative and noninvasive glucose measurements are taken at blocks 1102 and 1104, and the alternative measurement is output at block 1106. Likewise, a new noninvasive glucose value is determined at block 1108.

At decision block 1110, it is determined whether a difference between new and first noninvasive values exceeds a threshold. If so, an alarm can be output at block 1112 indicating that a new alternative glucose measurement should be obtained, as in the process 1000. If not, it is further determined at decision block 1114 whether an elapsed time has exceeded a threshold. If so, then the alarm is output at block 1112. Thus, in certain embodiments, an alarm is triggered by elapsed time, even when the noninvasive value has not changed beyond a threshold.

In an alternative embodiment, instead of determining whether the noninvasive measurement differs more than a threshold, an elapse of time can be the main or only criteria used to determine whether to trigger an alarm. For example, a periodic time interval could be set for recommending an alternative measurement. Additionally, in alternative embodiments, the noninvasive value can be output instead of or in addition to the alternative value.

Figure 11B:
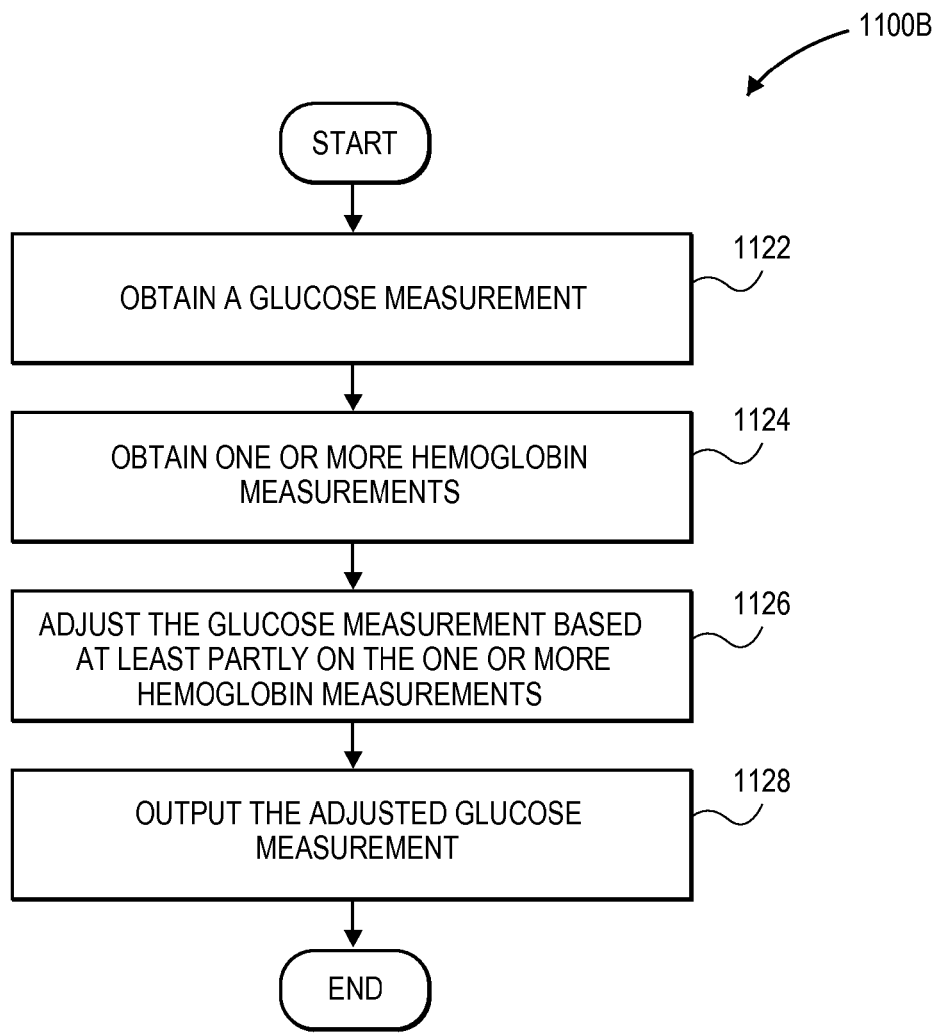
FIG. 11B illustrates an embodiment of a process for adjusting an alternative glucose measurement based at least in part on a hemoglobin measurement.

FIG. 11B illustrates an embodiment of a process 1100B for adjusting a glucose measurement. Test strips for finger-prick glucose meters can be sensitive to different concentrations of various hemoglobin species in an individual's blood. To compensate for these variations in hemoglobin species, in certain embodiments, the process 1100B adjusts glucose measurements based on one or more hemoglobin measurements. These features can also be applied to adjust noninvasive glucose measurements. The process 1100B can be implemented by the parameter calculator 101 or by another physiological monitor.

At block 1122, a glucose measurement is obtained. The glucose measurement can be invasive or noninvasive. At block 1124, one or more hemoglobin measurements are obtained. The hemoglobin measurements may include any of total hemoglobin (Hbt), methemoglobin, carboxyhemoglobin, or other hemoglobin species. The noninvasive sensor described above with respect to FIG. 4 could obtain these measurements. A more detailed example of a sensor for obtaining these measurements is described in U.S. Publication No. 2006/0211924, filed Mar. 1, 2006, titled "Multiple Wavelength Sensor Emitters," the disclosure of which is hereby incorporated by reference in its entirety.

The glucose measurement is adjusted at block 1126 based at least partly on the one or more hemoglobin measurements. In certain embodiments, this block 1126 can further include generating or modifying a calibration curve that relates glucose and one or more hemoglobin species. Like the calibration curve adjustments described above, an initial calibration curve relating glucose and hemoglobin species can be derived empirically. Then, at block 1126, the calibration curve can be adjusted based at least partly on the measurements of the hemoglobin species, thereby adjusting the glucose measurement. The adjustment of the glucose/hemoglobin calibration curve can be performed using any of the techniques described above, including adjusting weights of basis functions, using an adaptive algorithm, and so forth. At block 1128, the adjusted glucose measurement is output. For example, the adjusted glucose measurement can be output on a display.

In some embodiments, the process 1100B can be used to adjust noninvasive glucose measurements based on hemoglobin species. Moreover, an invasive/minimally-invasive glucose measurement can be adjusted based on hemoglobin measurements, and the adjusted invasive/minimally-invasive measurement can be supplied to any of the adaptive glucose algorithms described above. In one embodiment, a test strip glucose reader can be made more accurate by accounting for changes in hemoglobin species. In addition, rather than displaying a noninvasive glucose measurement, an invasive or minimally-invasive glucose measurement adjusted for hemoglobin species can be displayed. Moreover, in yet another embodiment, the monitor includes a strip reader and a hemoglobin sensor but not a noninvasive glucose sensor. Many other configurations are possible.

Figure 12:
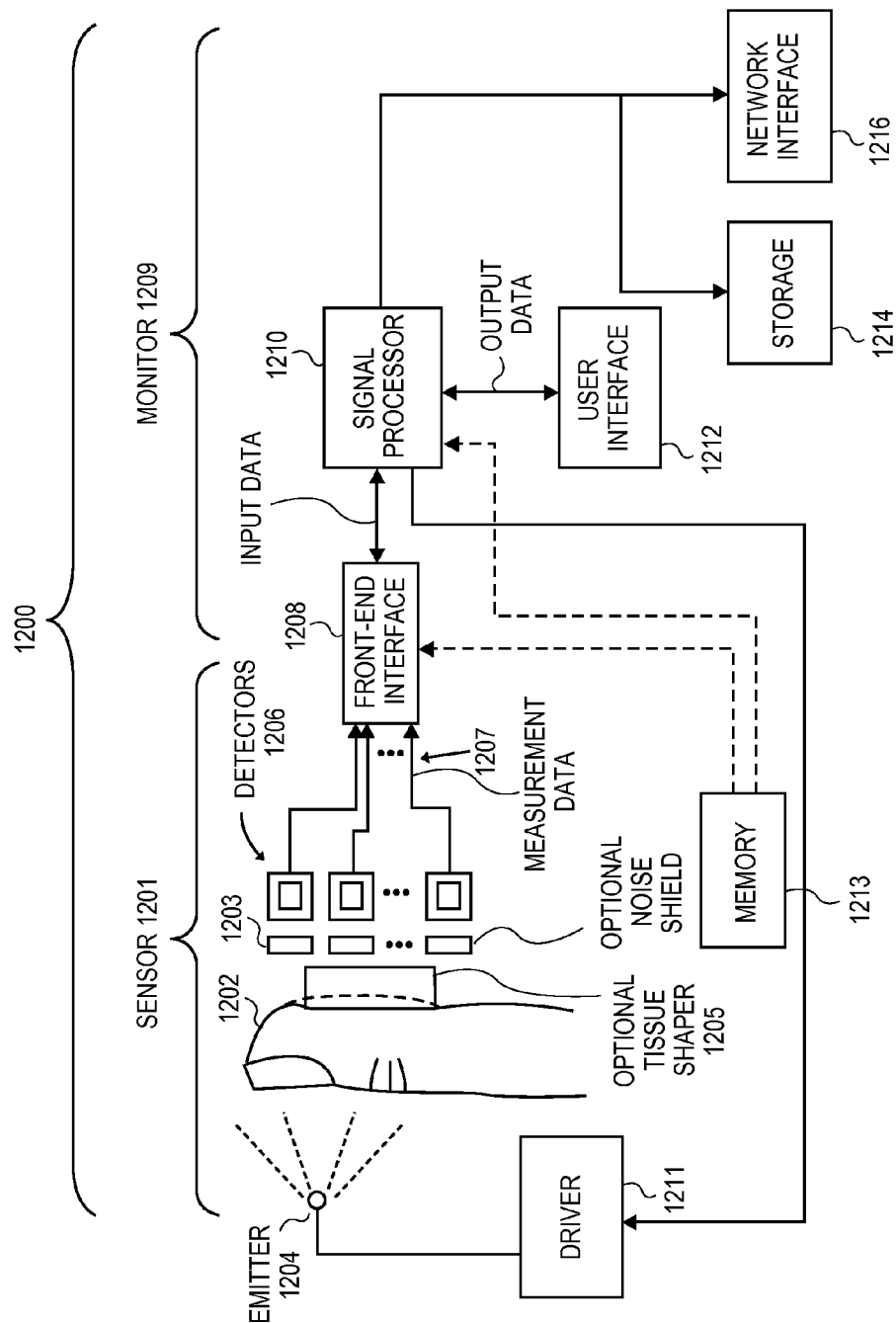
FIG. 12 illustrates another embodiment of a data collection system.

FIG. 12 illustrates an example of a data collection system 1200. In certain embodiments, the data collection system 1200 noninvasively measures a blood analyte, such as oxygen, carbon monoxide, methemoglobin, total hemoglobin, glucose, proteins, glucose, lipids, a percentage thereof (e.g., saturation) or one or more other physiologically relevant patient characteristics. The system 1200 can also measure additional blood constituents or analytes and/or other physiological parameters useful in determining a state or trend of wellness of a patient.

The data collection system 1200 can be capable of measuring optical radiation from the measurement site. For example, in some embodiments, the data collection system 1200 can employ one or more photodiodes. In an embodiment, the photodiodes have an area from about 1 $mm^2$-5 $mm^2$ (or higher) and are capable of detecting about 100 nanoamps (nA) or less of current resulting from measured light at full scale. In addition to having its ordinary meaning, the phrase "at full scale" can mean light saturation of a photodiode amplifier (not shown). Of course, other sizes and types of photodiodes can be used in various embodiments.

The data collection system 1200 can measure a range of approximately about 2 nA to about 100 nA or more full scale. The data collection system 1200 can also include sensor front-ends that are capable of processing and amplifying current from the detector(s) at signal-to-noise ratios (SNRs) of about 100 decibels (dB) or more, such as about 120 dB in order to measure various desired analytes. The data collection system 1200 can operate with a lower SNR if less accuracy is desired for an analyte like glucose.

The data collection system 1200 can measure analyte concentrations, including glucose, at least in part by detecting light attenuated by a measurement site 1202. The measurement site 1202 can be any location on a patient's body, such as a finger, foot, ear lobe, or the like. For convenience, this disclosure is described primarily in the context of a finger measurement site 1202. However, the features of the embodiments disclosed herein can be used with other measurement sites 1202.

In the depicted embodiment, the system 1200 includes an optional tissue thickness adjuster or tissue shaper 1205, which can include one or more protrusions, bumps, lenses, or other suitable tissue-shaping mechanisms. In certain embodiments, the tissue shaper 1205 is a flat or substantially flat surface that can be positioned proximate the measurement site 1202 and that can apply sufficient pressure to cause the tissue of the measurement site 1202 to be flat or substantially flat. In other embodiments, the tissue shaper 1205 is a convex or substantially convex surface with respect to the measurement site 1202. Many other configurations of the tissue shaper 1205 are possible. Advantageously, in certain embodiments, the tissue shaper 1205 reduces thickness of the measurement site 1202 while preventing or reducing occlusion at the measurement site 1202. Reducing thickness of the site can advantageously reduce the amount of attenuation of the light because there is less tissue through which the light must travel. Shaping the tissue in to a convex (or alternatively concave) surface can also provide more surface area from which light can be detected.

The embodiment of the data collection system 1200 shown also includes an optional noise shield 1203. In an embodiment, the noise shield 1203 can be advantageously adapted to reduce electromagnetic noise while increasing the transmittance of light from the measurement site 1202 to one or more detectors 1206 (described below). For example, the noise shield 1203 can advantageously include one or more layers of conductive coated glass or a metal grid electrically communicating with one or more other shields of the sensor 1201 or electrically grounded. In an embodiment where the noise shield 1203 includes conductive coated glass, the coating can advantageously include indium tin oxide. In an embodiment, the indium tin oxide includes a surface resistivity ranging from approximately 30 ohms per square inch to about 500 ohms per square inch. In an embodiment, the resistivity is approximately 30, 200, or 500 ohms per square inch. Other resistivities can also be used which are less than about 30 ohms or more than about 500 ohms. Other conductive materials that are transparent or substantially transparent to light can be used instead.

In some embodiments, the measurement site 1202 is located somewhere along a non-dominant arm or a non-dominant hand, e.g., a right-handed person's left arm or left hand. In some patients, the non-dominant arm or hand can have less musculature and higher fat content, which can result in less water content in that tissue of the patient. Tissue having less water content can provide less interference with the particular wavelengths that are absorbed in a useful manner by blood analytes like glucose. Accordingly, in some embodiments, the data collection system 1200 can be used on a person's non-dominant hand or arm.

The data collection system 1200 can include a sensor 1201 (or multiple sensors) that is coupled to a processing device or physiological monitor 1209. In an embodiment, the sensor 1201 and the monitor 1209 are integrated together into a single unit. In another embodiment, the sensor 1201 and the monitor 1209 are separate from each other and communicate one with another in any suitable manner, such as via a wired or wireless connection. The sensor 1201 and monitor 1209 can be attachable and detachable from each other for the convenience of the user or caregiver, for ease of storage, sterility issues, or the like. The sensor 1201 and the monitor 1209 will now be further described.

In the depicted embodiment shown in FIG. 12, the sensor 1201 includes an emitter 1204, an optional tissue shaper 1205, a set of detectors 1206, and a front-end interface 1208. The emitter 1204 can serve as the source of optical radiation transmitted towards measurement site 1202. As will be described in further detail below, the emitter 1204 can include one or more sources of optical radiation, such as LEDs, laser diodes, incandescent bulbs with appropriate frequency-selective filters, combinations of the same, or the like. In an embodiment, the emitter 1204 includes sets of optical sources that are capable of emitting visible and near-infrared optical radiation.

In some embodiments, the emitter 1204 is used as a point optical source, and thus, the one or more optical sources of the emitter 1204 can be located within a close distance to each other, such as within about a 2 mm to about 4 mm. The emitters 1204 can be arranged in an array, such as is described in U.S. Publication No. 2006/0211924, filed Sep. 21, 2006, titled "Multiple Wavelength Sensor Emitters," the disclosure of which is hereby incorporated by reference in its entirety. In particular, the emitters 1204 can be arranged at least in part as described in paragraphs [0061] through [0068] of the aforementioned publication, which paragraphs are hereby incorporated specifically by reference. Other relative spatial relationships can be used to arrange the emitters 1204.

For analytes like glucose, currently available non-invasive techniques often attempt to employ light near the water absorbance minima at or about 1600 nm. Typically, these devices and methods employ a single wavelength or single band of wavelengths at or about 1600 nm. However, to date, these techniques have been unable to adequately consistently measure analytes like glucose based on spectroscopy.

In contrast, the emitter 1204 of the data collection system 1200 can emit, in certain embodiments, combinations of optical radiation in various bands of interest. For example, in some embodiments, for analytes like glucose, the emitter 1204 can emit optical radiation at three (3) or more wavelengths between about 1600 nm to about 1700 nm. In particular, the emitter 1204 can emit optical radiation at or about 1610 nm, about 1640 nm, and about 1665 nm. In some circumstances, the use of three wavelengths within about 1600 nm to about 1700 nm enable sufficient SNRs of about 100 dB, which can result in a measurement accuracy of about 20 mg/dL or better for analytes like glucose.

In other embodiments, the emitter 1204 can use two (2) wavelengths within about 1600 nm to about 1700 nm to advantageously enable SNRs of about 85 dB, which can result in a measurement accuracy of about 25-30 mg/dL or better for analytes like glucose. Furthermore, in some embodiments, the emitter 1204 can emit light at wavelengths above about 1670 nm. Measurements at these wavelengths can be advantageously used to compensate or confirm the contribution of protein, water, and other non-hemoglobin species exhibited in measurements for analytes like glucose conducted between about 1600 nm and about 1700 nm. Of course, other wavelengths and combinations of wavelengths can be used to measure analytes and/or to distinguish other types of tissue, fluids, tissue properties, fluid properties, combinations of the same or the like.

For example, the emitter 1204 can emit optical radiation across other spectra for other analytes. In particular, the emitter 1204 can employ light wavelengths to measure various blood analytes or percentages (e.g., saturation) thereof. For example, in one embodiment, the emitter 1204 can emit optical radiation in the form of pulses at wavelengths of about 905 nm, about 1050 nm, about 1200 nm, about 1300 nm, about 1330 nm, about 1610 nm, about 1640 nm, and/or about 1665 nm. In another embodiment, the emitter 1204 can emit optical radiation ranging from about 860 nm to about 950 nm, about 950 nm to about 1100 nm, about 1100 nm to about 1270 nm, about 1250 nm to about 1350 nm, about 1300 nm to about 1360 nm, and/or about 1590 nm to about 1700 nm. Of course, the emitter 1204 can transmit any of a variety of wavelengths of visible or near-infrared optical radiation.

Due to the different responses of analytes to the different wavelengths, certain embodiments of the data collection system 1200 can advantageously use the measurements at these different wavelengths to improve the accuracy of measurements. For example, the measurements of water from visible and infrared light can be used to compensate for water absorbance that is exhibited in the near-infrared wavelengths.

As briefly described above, the emitter 1204 can include sets of light-emitting diodes (LEDs) as its optical source. The emitter 1204 can use one or more top-emitting LEDs. In particular, in some embodiments, the emitter 1204 can include top-emitting LEDs emitting light at about 850 nm to 1350 nm.

The emitter 1204 can also use super luminescent LEDs (SLEDs) or side-emitting LEDs. In some embodiments, the emitter 1204 can employ SLEDs or side-emitting LEDs to emit optical radiation at about 1600 nm to about 1800 nm. Emitter 1204 can use SLEDs or side-emitting LEDs to transmit near infrared optical radiation because these types of sources can transmit at high power or relatively high power, e.g., about 40 mW to about 100 mW. This higher power capability can be useful to compensate or overcome the greater attenuation of these wavelengths of light in tissue and water. For example, the higher power emission can effectively compensate and/or normalize the absorption signal for light in the mentioned wavelengths to be similar in amplitude and/or effect as other wavelengths that can be detected by one or more photodetectors after absorption. However, certain embodiments do not necessarily require the use of high power optical sources. For example, some embodiments may be configured to measure analytes, such as total hemoglobin (tHb), oxygen saturation ($SpO_2$), carboxyhemoglobin, methemoglobin, etc., without the use of high power optical sources like side emitting LEDs. Instead, such embodiments may employ other types of optical sources, such as top emitting LEDs. Alternatively, the emitter 1204 can use other types of sources of optical radiation, such as a laser diode, to emit near-infrared light into the measurement site 1202.

In addition, in some embodiments, in order to assist in achieving a comparative balance of desired power output between the LEDs, some of the LEDs in the emitter 1204 can have a filter or covering that reduces and/or cleans the optical radiation from particular LEDs or groups of LEDs. For example, since some wavelengths of light can penetrate through tissue relatively well, LEDs, such as some or all of the top-emitting LEDs can use a filter or covering, such as a cap or painted dye. This can be useful in allowing the emitter 1204 to use LEDs with a higher output and/or to equalize intensity of LEDs.

The data collection system 1200 also includes a driver 1211 that drives the emitter 1204. The driver 1211 can be a circuit or the like that is controlled by the monitor 1209. For example, the driver 1211 can provide pulses of current to the emitter 1204. In an embodiment, the driver 1211 drives the emitter 1204 in a progressive fashion, such as in an alternating manner. The driver 1211 can drive the emitter 1204 with a series of pulses of about 1 milliwatt (mW) for some wavelengths that can penetrate tissue relatively well and from about 40 mW to about 100 mW for other wavelengths that tend to be significantly absorbed in tissue. A wide variety of other driving powers and driving methodologies can be used in various embodiments.

The driver 1211 can be synchronized with other parts of the sensor 1201 and can minimize or reduce jitter in the timing of pulses of optical radiation emitted from the emitter 1204. In some embodiments, the driver 1211 is capable of driving the emitter 1204 to emit optical radiation in a pattern that varies by less than about 10 parts-per-million.

The detectors 1206 capture and measure light from the measurement site 1202. For example, the detectors 1206 can capture and measure light transmitted from the emitter 1204 that has been attenuated or reflected from the tissue in the measurement site 1202. The detectors 1206 can output a detector signal 1207 responsive to the light captured or measured. The detectors 1206 can be implemented using one or more photodiodes, phototransistors, or the like.

In addition, the detectors 1206 can be arranged with a spatial configuration to provide a variation of path lengths among at least some of the detectors 1206. That is, some of the detectors 1206 can have the substantially, or from the perspective of the processing algorithm, effectively, the same path length from the emitter 1204. However, according to an embodiment, at least some of the detectors 1206 can have a different path length from the emitter 1204 relative to other of the detectors 1206. Variations in path lengths can be helpful in allowing the use of a bulk signal stream from the detectors 1206. In some embodiments, the detectors 1206 may employ a linear spacing, a logarithmic spacing, or a two or three dimensional matrix of spacing, or any other spacing scheme in order to provide an appropriate variation in path lengths.

The front end interface 1208 provides an interface that adapts the output of the detectors 1206, which is responsive to desired physiological parameters. For example, the front end interface 1208 can adapt a signal 1207 received from one or more of the detectors 1206 into a form that can be processed by the monitor 1209, for example, by a signal processor 1210 in the monitor 1209. The front end interface 1208 can have its components assembled in the sensor 1201, in the monitor 1209, in connecting cabling (if used), combinations of the same, or the like. The location of the front end interface 1208 can be chosen based on various factors including space desired for components, desired noise reductions or limits, desired heat reductions or limits, and the like.

The front end interface 1208 can be coupled to the detectors 1206 and to the signal processor 1210 using a bus, wire, electrical or optical cable, flex circuit, or some other form of signal connection. The front end interface 1208 can also be at least partially integrated with various components, such as the detectors 1206. For example, the front end interface 1208 can include one or more integrated circuits that are on the same circuit board as the detectors 1206. Other configurations can also be used.

The front end interface 1208 can be implemented using one or more amplifiers, such as transimpedance amplifiers, that are coupled to one or more analog to digital converters (ADCs) (which can be in the monitor 1209), such as a sigma-delta ADC. A transimpedance-based front end interface 1208 can employ single-ended circuitry, differential circuitry, and/or a hybrid configuration. A transimpedance-based front end interface 1208 can be useful for its sampling rate capability and freedom in modulation/demodulation algorithms. For example, this type of front end interface 1208 can advantageously facilitate the sampling of the ADCs being synchronized with the pulses emitted from the emitter 1204.

The ADC or ADCs can provide one or more outputs into multiple channels of digital information for processing by the signal processor 1210 of the monitor 1209. Each channel can correspond to a signal output from a detector 1206.

In some embodiments, a programmable gain amplifier (PGA) can be used in combination with a transimpedance-based front end interface 1208. For example, the output of a transimpedance-based front end interface 1208 can be output to a PGA that is coupled with an ADC in the monitor 1209. A PGA can be useful in order to provide another level of amplification and control of the stream of signals from the detectors 1206. Alternatively, the PGA and ADC components can be integrated with the transimpedance-based front end interface 1208 in the sensor 1201.

In another embodiment, the front end interface 1208 can be implemented using switched-capacitor circuits. A switched-capacitor-based front end interface 1208 can be useful for, in certain embodiments, its resistor-free design and analog averaging properties. In addition, a switched-capacitor-based front end interface 1208 can be useful because it can provide a digital signal to the signal processor 1210 in the monitor 1209.

As shown in FIG. 12, the monitor 1209 can include the signal processor 1210 and a user interface, such as a display 1212. The monitor 1209 can also include optional outputs alone or in combination with the display 1212, such as a storage device 1214 and a network interface 1216. In an embodiment, the signal processor 1210 includes processing logic that determines measurements for desired analytes, such as glucose, based on the signals received from the detectors 1206. The signal processor 1210 can be implemented using one or more microprocessors or subprocessors (e.g., cores), digital signal processors, application specific integrated circuits (ASICs), field programmable gate arrays (FPGAs), combinations of the same, and the like.

The signal processor 1210 can provide various signals that control the operation of the sensor 1201. For example, the signal processor 1210 can provide an emitter control signal to the driver 1211. This control signal can be useful in order to synchronize, minimize, or reduce jitter in the timing of pulses emitted from the emitter 1204. Accordingly, this control signal can be useful in order to cause optical radiation pulses emitted from the emitter 1204 to follow a precise timing and consistent pattern. For example, when a transimpedance-based front end interface 1208 is used, the control signal from the signal processor 1210 can provide synchronization with the ADC in order to avoid aliasing, cross-talk, and the like. As also shown, an optional memory 1213 can be included in the front-end interface 1208 and/or in the signal processor 1210. This memory 1213 can serve as a buffer or storage location for the front-end interface 1208 and/or the signal processor 1210, among other uses.

The user interface 1212 can provide an output, e.g., on a display, for presentation to a user of the data collection system 1200. The user interface 1212 can be implemented as a touch-screen display, an LCD display, an organic LED display, or the like. In addition, the user interface 1212 can be manipulated to allow for measurement on the non-dominant side of patient. For example, the user interface 1212 can include a flip screen, a screen that can be moved from one side to another on the monitor 1209, or can include an ability to reorient its display indicia responsive to user input or device orientation. In alternative embodiments, the data collection system 1200 can be provided without a user interface 1212 and can simply provide an output signal to a separate display or system.

A storage device 1214 and a network interface 1216 represent other optional output connections that can be included in the monitor 1209. The storage device 1214 can include any computer-readable medium, such as a memory device, hard disk storage, EEPROM, flash drive, or the like. The various software and/or firmware applications can be stored in the storage device 1214, which can be executed by the signal processor 1210 or another processor of the monitor 1209. The network interface 1216 can be a serial bus port (RS-232/RS-485), a Universal Serial Bus (USB) port, an Ethernet port, a wireless interface (e.g., WiFi such as any 802.1x interface, including an internal wireless card), or other suitable communication device(s) that allows the monitor 1209 to communicate and share data with other devices. The monitor 1209 can also include various other components not shown, such as a microprocessor, graphics processor, or controller to output the user interface 1212, to control data communications, to compute data trending, or to perform other operations.

Although not shown in the depicted embodiment, the data collection system 1200 can include various other components or can be configured in different ways. For example, the sensor 1201 can have both the emitter 1204 and detectors 1206 on the same side of the measurement site 1202 and use reflectance to measure analytes. The data collection system 1200 can also include a sensor that measures the power of light emitted from the emitter 1204.

Depending on the embodiment, certain acts, events, or functions of any of the algorithms described herein can be performed in a different sequence, can be added, merged, or left out all together (e.g., not all described acts or events are necessary for the practice of the algorithm). Moreover, in certain embodiments, acts or events can be performed concurrently, e.g., through multi-threaded processing, interrupt processing, or multiple processors or processor cores, rather than sequentially.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a processor, controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of processor-readable or computer-readable storage medium known in the art. An exemplary storage medium can be coupled to the processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. A device capable of producing a signal responsive to light attenuated by tissue at a measurement site, the device comprising:
    an optical sensor configured to emit light on tissue of a living person, detect the light after attenuation by the tissue, and output a signal responsive to the attenuated light; and
    a processor configured to:
        receive the signal from the optical sensor;
        process the signal with a measurement algorithm to determine a first measurement of a physiological parameter, wherein the physiological parameter is glucose, and wherein the measurement algorithm comprises a plurality of basis functions and associated weights, wherein the measurement algorithm is configured to apply a combination of the basis functions and the weights to the signal to determine the first measurement,
        receive a second measurement of the physiological parameter from an alternative source, the second measurement being an invasive or minimally-invasive glucose measurement, and
        adaptively adjust the measurement algorithm based at least partly on the second measurement by adapting the weights of the measurement algorithm.

2. The device of claim 1, wherein the processor is further configured to adaptively adjust the measurement algorithm by adjusting a calibration curve associated with the measurement algorithm.

3. The device of claim 1, wherein the alternative source comprises an invasive measurement device.

4. The device of claim 1, wherein the alternative source comprises a minimally-invasive measurement device.

5. The device of claim 1, wherein the alternative source comprises a finger-prick device.

6. The device of claim 1, wherein the alternative source comprises an input of the second measurement provided by the living person.

7. A device capable of producing a signal responsive to light attenuated by tissue at a measurement site, the device comprising:
    a processor configured to:
        receive a signal from an optical sensor, the signal representing physiological information of a patient;
        process the signal with a measurement algorithm to determine a first measurement of a physiological parameter, wherein the physiological parameter is glucose, and wherein the measurement algorithm comprises a plurality of basis functions and associated weights, wherein the measurement algorithm is configured to apply a combination of the basis functions and the weights to the signal to determine the first measurement;
        receive a second measurement of the physiological parameter from an alternative source, the second measurement being an invasive or minimally-invasive glucose measurement; and
        adaptively adjust the measurement algorithm based at least partly on the second measurement by adapting the weights of the measurement algorithm.

8. The device of claim 7, wherein the processor is further configured to adaptively adjust the measurement algorithm by adjusting a calibration curve associated with the measurement algorithm.

9. The device of claim 7, wherein the alternative source comprises an invasive measurement device.

10. The device of claim 7, wherein the alternative source comprises a minimally-invasive measurement device.

11. The device of claim 7, wherein the alternative source comprises a finger-prick device.

12. The device of claim 7, wherein the alternative source comprises an input of the second measurement provided by the patient.

13. A method of producing a signal responsive to light attenuated by tissue at a measurement site, the method comprising:
    receiving a signal from an optical sensor, the signal representing physiological information of a patient;
    processing the signal with a measurement algorithm, by one or more processors, to determine a first measurement of a physiological parameter, wherein the physiological parameter is glucose, and wherein the measurement algorithm comprises a plurality of basis functions and associated weights, wherein the measurement algorithm is configured to apply a combination of the basis functions and the weights to the signal to determine the first measurement;
    receiving a second measurement of the physiological parameter from an alternative source, the second measurement being an invasive or minimally-invasive glucose measurement; and
    adaptively adjusting the measurement algorithm based at least partly on the second measurement by adapting the weights of the measurement algorithm.

14. The method of claim 13, wherein the processor is further configured to adaptively adjust the measurement algorithm by adjusting a calibration curve associated with the measurement algorithm.

15. The method of claim 13, wherein the alternative source comprises an invasive measurement device.

16. The method of claim 13, wherein the alternative source comprises a minimally-invasive measurement device.

17. The method of claim 13, wherein the alternative source comprises a finger-prick device.

18. The method of claim 13, wherein the alternative source comprises an input of the second measurement provided by the patient.

\* \* \* \* \*